US011160834B2

(12) United States Patent
Prockop et al.

(10) Patent No.: US 11,160,834 B2
(45) Date of Patent: Nov. 2, 2021

(54) SCALABLE PRODUCTION OF STANDARDIZED EXTRACELLULAR VESICLES, EXTRACELLULAR VESICLE PREPARATIONS AND USES THEREOF

(71) Applicant: THE TEXAS A&M UNIVERSITY SYSTEM, College Station, TX (US)

(72) Inventors: Darwin J. Prockop, Philadelphia, PA (US); Dong-Ki Kim, College Station, TX (US); Hidetaka Nishida, College Station, TX (US); Askok K. Shetty, Austin, TX (US)

(73) Assignee: THE TEXAS A&M UNIVERSITY SYSTEM, College Station, TX (US)

(*) Notice: Subject to any disclaimer, the term of this patent is extended or adjusted under 35 U.S.C. 154(b) by 129 days.

(21) Appl. No.: 15/570,316

(22) PCT Filed: Apr. 28, 2016

(86) PCT No.: PCT/US2016/029874
§ 371 (c)(1),
(2) Date: Oct. 27, 2017

(87) PCT Pub. No.: WO2016/176500
PCT Pub. Date: Nov. 3, 2016

(65) Prior Publication Data
US 2018/0353548 A1 Dec. 13, 2018

Related U.S. Application Data

(60) Provisional application No. 62/153,846, filed on Apr. 28, 2015.

(51) Int. Cl.
*A61K 35/28* (2015.01)
*C12N 5/0775* (2010.01)
*A61K 35/12* (2015.01)
*A61P 43/00* (2006.01)
*A61P 29/00* (2006.01)
*C07K 5/062* (2006.01)
*A61K 9/00* (2006.01)

(52) U.S. Cl.
CPC ............ *A61K 35/28* (2013.01); *A61K 35/12* (2013.01); *A61P 29/00* (2018.01); *A61P 43/00* (2018.01); *C07K 5/06034* (2013.01); *C12N 5/0663* (2013.01); *A61K 9/0019* (2013.01); *C12N 2500/95* (2013.01)

(58) Field of Classification Search
CPC ...... A61K 35/28; A61K 35/12; A61K 9/0019; A61P 43/00; A61P 29/00; C07K 5/06034; C12N 5/0663; C12N 2500/95
USPC ...................................................... 424/93.7
See application file for complete search history.

(56) References Cited

U.S. PATENT DOCUMENTS

2003/0118567 A1  6/2003 Stewart
2012/0269774 A1  10/2012 Ichim et al.

FOREIGN PATENT DOCUMENTS

WO  2012-087241 A1  6/2012
WO  2012-125471 A1  9/2012
WO  2013-142878 A1  9/2013
WO  2015-016761 A2  2/2015

OTHER PUBLICATIONS

Zhang et al., Effect of exosomes derived from multipotent mesenchymal stromal cells on functional recovery and neurovascular plasticity in rats after traumatic brain injury, Journal of Neurosurgery, Published online Jan. 16, 2015, 122(4): p. 856-867.*
Sancho-Albero et al., Exosome origin determines cell targeting and the transfer of therapeutic nanoparticles towards target cells, Journal of Nanobiotechnology, (2019), 17(16): p. 1-13.*
Ghosh, et. al., Rapid Isolation of Extracellular Vesicles From Cell Culture and Biological Fluids Using a Synthetic Peptide with Specific Affinity for Heat Shock Proteins, PlOS One, Oct. 2014, pp. 1-12, vol. 9, Issue 10.
Kim, et. al., Chromatographically isolated CD63+CD81+ extracellular vesicles from mesenchymal stromal cells rescue cognitive impairments after TBI, PNAS, Jan. 5, 2016, pp. 170-175, vol. 113, No. 1.
International Search Report, dated Oct. 12, 2016, 5 pages.
Zhang et al., *Neurochem Int* 111:69-81 (Dec. 2017) [Zhang-2].
Hmler, *Nat Rev Drug Discov* 7(9):747-758 (Sep. 2008).

(Continued)

*Primary Examiner* — Jennifer M. H. Tichy
(74) *Attorney, Agent, or Firm* — Husch Blackwell LLP

(57) ABSTRACT

Preparations comprising an enriched population of extracellular vesicles (nEVs) having a negatively charged surface, and that are CD81+ and CD9−, are provided. Improved processes and methods for producing an enriched population of nEVs from non-murine cells, especially human origin cells and/or tissues, are disclosed. Therapeutic methods for using the preparations, including for reducing brain inflammation and treatment of various pathologies associated with brain inflammation, such as by intravenous or intranasal administration, are also described. Methods and preparations for reducing brain inflammation associated with traumatic brain injury (TBI) are also disclosed. A method for treating a patient having suffered a mild traumatic injury (mTMI), or concussion, such as a sports-related head injury, is also disclosed. The nEVs are also demonstrated to reduce the expression level of IL-1β in brain tissue of an animal having had traumatic brain injury. Methods for improving cognitive function and performance in animals after a traumatic brain injury is also demonstrated using the preparations of nEVs disclosed herein.

10 Claims, 36 Drawing Sheets

(56) References Cited

OTHER PUBLICATIONS

Midekessa et al., *ACS Omega* 5:16701-16710 (2020).
Machado-Pineda et al., *Front Immunol* 9:2474.(Nov. 2018).
Miki et al., *BJ Cancer* 118:867-877(Feb. 2018).
Blake et al., *Cytokine* 111:567-5570 (Nov. 2018).
Khabai et al., *Cell Transplant* 24(5):819-828 (2015).

* cited by examiner

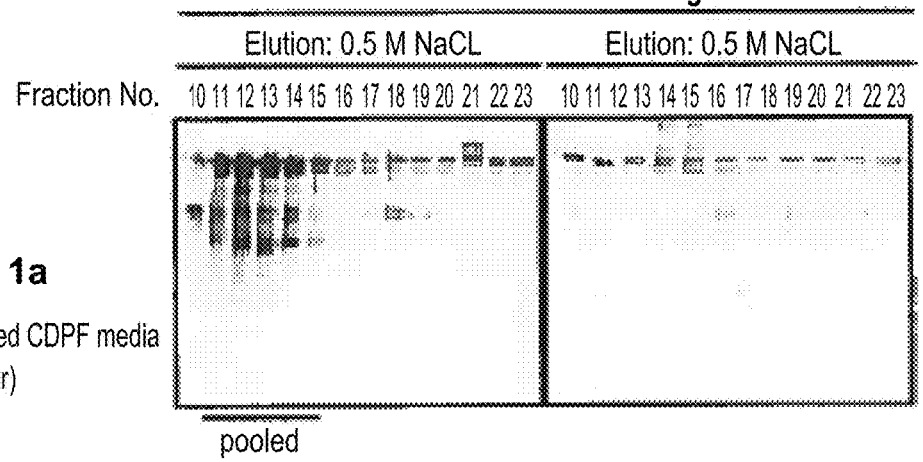
Figure 1b
Figure 1a
1.2 L of hMSCs-cultured CDPF media (6hr-48hr)
↓
Centrifugation, x 2.465 g, 15 min.
↓
Supernatant
↓
0.22 μm filtration
↓
Strong Anion exchange column, Express Q
↓
Wash with 0.05 M NaCl (20 column vol.)
↓
Elution with 0.5 M or 1.0 M NaCl (2 column vol.)
↓
Pooling the peak fractions
↓
Dialysis against PBS
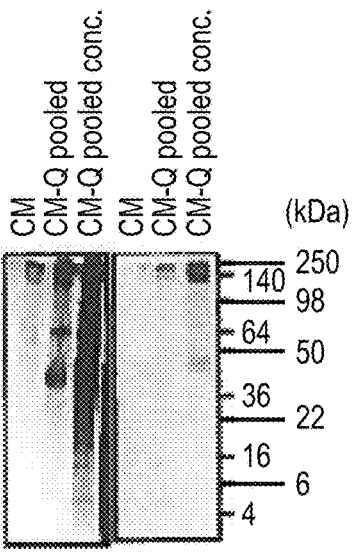
Figure 1c

Pooled CM-Q fractions

Figure 11a
BM-hMSC(#6015, P4 cultured media, 2.4 L)
↓
1st Anion Column: Concentration
(Eluted with 0.5 M NaCl)
↓
2nd Anion column: Separation
(Stepwise eluted with NaCl)
Figure 11b
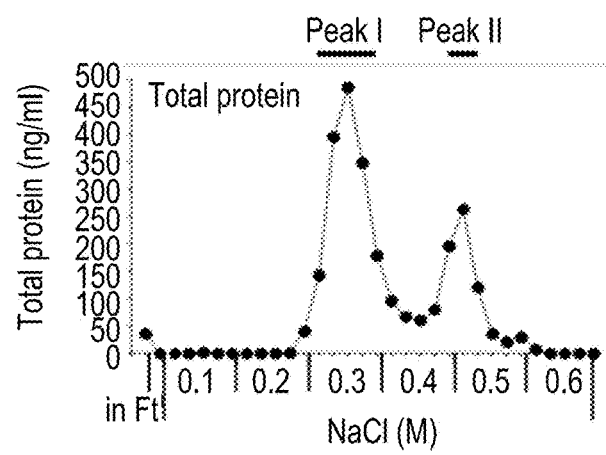
Figure 11c
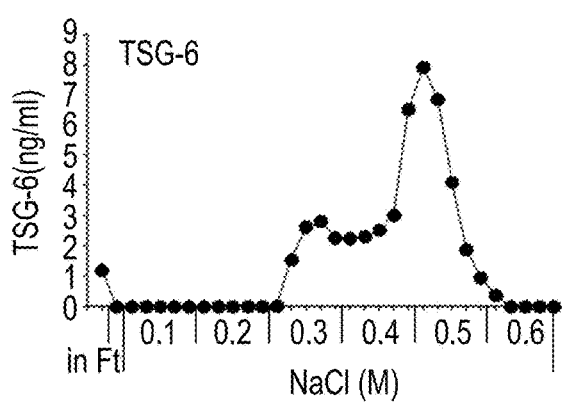
Figure 11d
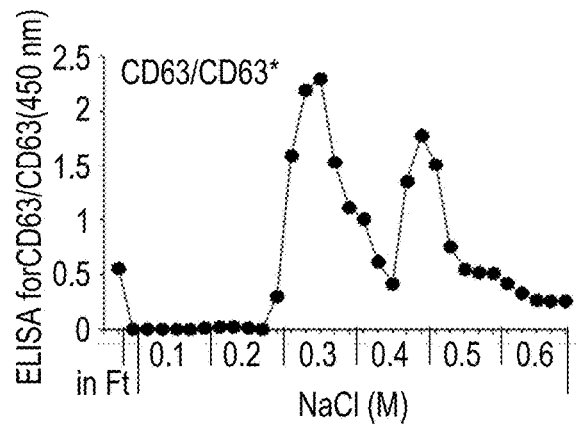

Silver stain

WB: copGFP

WB: cytosine deaminase

Figure 14b(ii)

Silver stain

SCALABLE PRODUCTION OF STANDARDIZED EXTRACELLULAR VESICLES, EXTRACELLULAR VESICLE PREPARATIONS AND USES THEREOF

CROSS-REFERENCE TO RELATED APPLICATIONS

The present application claims priority to U.S. Provisional Application Ser. No. 62/153,846, filed on Apr. 28, 2015.

STATEMENT OF GOVERNMENT SUPPORT

This invention was made with United States government funded support under NIH grant, NIH P40OD01105 23-461183. The United States government owns rights in the present invention.

FIELD OF THE INVENTION

The present invention relates to the field of preparations of extracellular vesicles, as preparations of negatively charged extracellular vesicles produced by mesenchymal stem cells (MSCs), having defined and reproducible properties, are provided. The present invention also relates to therapeutic methods, as therapeutic methods for treating and/or preventing inflammation, including brain inflammation and/or progressive brain damage attendant traumatic brain injury, is described. Methods for treating mild TBI, as well as other pathologies associated with brain inflammation (such as concussion) in a patient are also provided. The present invention also relates to the field of cognitive brain function and memory loss, as preparations and methods for treating pathologies associated with loss of cognitive brain function, Alzheimer's Disease, dementia, and brain function attendant traumatic brain injury, are provided.

BACKGROUND OF THE INVENTION

Recent publications have established that extracellular vesicles (EVs) released by specific populations of cells have therapeutic effects in animal models for human diseases. This observation may be related to the presence of therapeutic proteins and micro-RNAs in the EVs. It has been reported that mesenchymal stem/stromal cells are an attractive source of EVs, and they may possess therapeutic effects for some specifically defined conditions (stroke, kidney failure, diabetes, Parkinson's Disease, myocardial infarction, multiple sclerosis, and graft versus host disease).

There is a pressing need for more effective methods and drugs for treating inflammatory disease and/or injury to tissue caused by inflammation, for example, that are better able to reach the brain; or with new mechanisms offering advantages over existing approaches. In particular, preparations and methods for treating brain inflammation, such as the brain inflammation that results from traumatic brain injury (TBI), mild traumatic brain injury (mTBI) and concussion, is not described, yet is seriously needed in the medical arts. An attendant and equally patient compromising condition that results from TBI is loss in cognitive function. Unfortunately, an effective medical and/or therapeutic approach for improving loss in cognitive function does not currently exist.

Despite preliminary results in animal models, significant challenges to the therapeutic application of EVs to human patients exist. For example, no efficient methodology and/or process exists to produce EVs of specifically identifiable and reproducible properties, and therefore an appropriate source for utilizing these materials in human pharmaceutical preparations is lacking. In addition, there remains a deficiency in the art for a clinically and/or pharmaceutically scalable process for producing uniform EV preparations. Current methods that rely primarily on centrifugation for isolation/purification of EVs are not easily scalable, and are less efficient for providing high yield EV product. Thus, there also remains a need in the medical arts for a scalable method whereby cells may be cultured to consistently and reliably produce a clinically relevant number of EVs, having defined and reproducible characteristics for pharmaceutical preparations.

With heightened awareness of concussion, there is a need to assess and manage the concussed patient in a consistent manner. Unfortunately, concussion physical examination has not been standardized or supported by evidence.

The present invention provides a solution to these and other problems in the prior art.

SUMMARY OF THE INVENTION

The present invention, in a general and overall sense, provides a preparation that is enriched for a defined population of negatively charged extracellular vesicles (n-EV), and particularly identified by the absence of a surface CD9 epitope (CD9). Methods for producing the defined population of the enriched n-EVs are also provided. In some embodiments, the enriched population of n-EVs may be isolated from materials produced by stem cells, such as mesenchymal stem cells and/or embryonic and/or undifferentiated stem cells, or by IPS cells.

The n-EVs are characterized as having a negative surface charge. The negative net surface charge of the n-EV-containing preparations is attributable, at least in part, to the presence of negatively charged phospholipids on the EV surface.

In some embodiments, the enriched population of n-EVs are identifiable by the detectable presence of a particular surface epitope or combination of surface epitopes, and/or by the absence of particular surface epitopes. For example, the present enriched population of n-EVs are characterized by the presence of vesicle surface detectable levels of the epitope CD63 (i.e., CD63(+)) and CD81 (i.e., CD81+), and by the surface absence of certain other surface detectable levels of the epitope CD9 (i.e., CD9⁻).

In other embodiments, the enriched population of n-EVs are negative for any detectable surface levels of all, or any combination of two (2) or more, of the following epitopes: CD29, CD44, CD49c, CD50, CD59, CD90, CD105, CD147, CD166, and HLA-1ABC. One or more of these surface epitopes are typically present in detectable levels on the surface of mesenchymal stem cells, and therefore the present preparation moieties, referred to as extracellular vesicles herein, may be distinguished based on the presence or absence of certain surface epitopes, and may also be used as a basis upon which the n-EV enriched population can be distinguished from other preparations. The absence of CD9 epitope on the surface of the preparations described herein also provides a point that separates the present enriched moiety preparations from other described EV preparations described. In addition, the enriched preparation of the n-EVs of the invention are distinct from the native population of EVs that originate from mesenchymal stem cells in vivo or from in vitro culture.

In particular embodiments, the enriched populations of n-EVs are absent detectable surface levels of (i.e., are negative for) the surface epitopes CD9, CD 29, CD44, CD49c, CD50, CD59, CD90, CD105, CD147, CD166, and HLA-1ABC.

In some embodiments, the n-EVs are prepared by culturing mesenchymal stem cells isolated from human bone marrow tissue. In particular embodiments, the bone marrow is human bone marrow and human bone marrow-derived mesenchymal stem cells are preselected for high expression of the biomarker TSG-6. TSG-6 has been reported to provide an indicator of efficacy for some populations of cells to suppress inflammation in mice. However, the present technology is not limited to the type of non-murine, and especially, human tissues from which a population of mesenchymal stem cells may be obtained, and subsequently cultured to provide a preparation that is enriched for a population surface negative extracellular vesicles (n-EVs) according to the present invention. For example, sources of non-murine mesenchymal stem cells may include, but are not limited to, human adipose tissue, human cord blood, human peripheral blood, human brain tissue, human spinal cord tissue, human blood vessels, human skeletal muscle tissue, human skin tissue, human tooth tissues, human gum tissue, human heart tissue, human intestinal tissue, human liver tissue, human ovarian epithelium, human amniotic fluid, human umbilical cord tissue, and human testicular tissue. Alternatively, the present preparations may be prepared from undifferentiated human stem cells, such as embryonic stem cells, that have been induced to a more mature, differentiated state, capable of being cultured under appropriate artificial conditions suitable for the production of the negatively charged phospholipid moieties (such as the n-EVs, extracellular vesicles) described herein.

In some embodiments, an "enriched" preparation of n-EVs, as that term is used in the present invention, may be defined as a preparation that comprises a greater weight percent and/or volume of human n-EVs (human cell and/or tissue origin EV's having a negative surface charge) prepared under defined conditions employing human cells and/or human tissues, compared to the weight percent and/or volume of EVs and/or exosomes prepared and/or isolated employing non-human cells and/or non-human tissues (e.g., murine cells and/or murine tissues (bone marrow)). The enriched n-EV preparations may be further described as having a CD64+ surface epitope, and as being CD9$^-$. Thus, the present n-EV preparations are readily distinguished from other native and/or non-human tissue and/or non-human cell generated EV preparations and exosome preparations. By way of further example, a preparation having an enriched population of n-EVs may be described as a preparation that comprises at least 50% or more (60%, 70%, 80% or up to 100%) n-EVs (negatively charges surface EVs) of human cell and/or tissue origin, compared to the percentage of exosomes or EVs in the preparation of a non-human cell and/or non-human tissue origin, and/or that carry a positive (+) surface charge.

In some embodiments, the "enriched" population of n-EVs may be further described as a preparation that comprises a greater volume (by weight) or percentage (greater than 50%) of n-EVs of human cell and/or human tissue origin, and/or that have not been modified (e.g., "loaded") ex vivo with one or more chemical or biologically active moieties (e.g., without catalase), compared to the volume or percentage of exosomes or extracellular vesicles that have been modified ex vivo and/or that are of a non-human cell (such as murine macrophages, murine monocytes, murine MSC) and/or non-human tissue (such as murine bone marrow) origin. It is contemplated that the n-EVs of human tissue and/or human cell origin of the present preparations may be modified to carry therapeutic and biologically active agents, but will be essentially free of extracellular vesicles and exosomes of non-human tissue and/or non-human cell origin, that have been modified to carry therapeutic and biologically active agents. In particular embodiments, the human n-EV preparations may be described as not having a sonication-induced surface modification. It has been reported that sonication will change the surface characteristics of murine cell secreted exosomes isolated in culture from murine bone marrow derived macrophages (Haney et al. (2015), J. of Controlled Release, 207:18-30).

In particular embodiments, an enriched preparation of human n-EVs comprises about 60% to about 95% of human tissue and/or human cell derived n-EVs by weight and/or volume of the preparation. In other embodiments, an enriched preparation of n-EVs comprises about 70% to about 90% n-EVs by weight and/or volume of the preparation.

Another aspect of the invention provides for a pharmaceutical preparation comprising the n-EVs in a pharmaceutically acceptable carrier solution. By way of example, the carrier solution is saline. In particular embodiments, the preparation will be suitable for intravenous administration or by intranasal administration, to an animal, such as a human.

Another aspect of the invention provides an improved and scalable method for producing an enriched population of negatively charged extracellular vesicles (n-EVs) of human cell and/or human tissue origin. In some embodiments, the method comprises culturing human mesenchymal stem cells in a protein-free, chemically defined culture medium to produce a conditioned culture medium; passing the conditioned culture medium over an anion exchange resin to provide an attached population of negatively charged extracellular vesicles; and collecting the population of negatively charged extracellular vesicles with an appropriate buffer, such as NACL, wherein the negatively charged extracellular vesicles are CD63$^+$ and CD9$^-$. The exchange resin will be eluted with a particular elution buffer and selected fractions of the eluate will be concentrated (e.g., by dialysis) to provide an enriched n-EV preparation. In particular embodiments, the anion exchange resin used in the scalable method is of a sufficient size to accommodate large scale volumes of conditioned culture media. In other embodiments of the method, a second elution of the collected fractions from a first passage over an anion exchange column may be performed. In collection of the resulting eluates, it has been found that a two separate peaks of identifiable protein containing eluates may be separated.

In yet another aspect, therapeutic methods using a pharmaceutical preparation of n-EVs are provided. In particular embodiments, a method for reducing inflammation in an animal (such as a human) with a pharmaceutical preparation of n-EVs is provided. In some embodiments, the method comprises administering a pharmaceutically acceptable preparation comprising negatively charged extracellular vesicles (n-EVs) to an animal at risk of or having inflammation, and observing a reduction in inflammation in the animal. In a particular embodiment, the inflammation is brain inflammation associated with traumatic brain injury (TBI). In a particular aspect, a reduction in inflammation may be correlated with a reduction in brain concentration levels or decreased synthesis/formation of IL-1β in the animal.

In yet another aspect, a method for treating a subject for concussion is provided employing the pharmaceutical preparations described herein.

In yet another aspect, a method of improving cognitive function in an animal suffering brain injury or loss of cognitive functions is provided. By way of example, brain inflammation occurs after several pathological events, including traumatic brain injury (TBI), mild traumatic brain injury (mTBI), and concussion. In some embodiments, the method comprises administering to the animal having experienced a brain inflammatory event, a therapeutically effective amount of the pharmaceutical preparation containing an enriched population of n-EVs (as described herein) in a pharmaceutically acceptable carrier solution. In particular embodiments, the preparation should be suitable for intravenous delivery or alternatively intranasal delivery to the animal, such as to a human.

The preparation of n-EVs provided as part of the present preparations are distinguishable from EVs produced by mesenchymal stem cells in vitro. Other preparations relating to moieties described as extracellular vesicles note those preparations have a positive (+) surface epitope for CD9, among other characteristics. In contrast, the n-EV preparations provided s part of the present preparations are absent a detectable positive (+) presence of CD9. Therefore, it is not anticipated that other EV preparations that are CD9+ demonstrate the potency of anti-inflammatory activity, or other characteristics, of the present preparations.

BRIEF DESCRIPTION OF THE DRAWINGS

FIG. 1a—Method for preparation of n-EVs from mesenchymal stem cells. The cells were from a normal human donor, and the cells were preselected for expression of a biomarker TSG-6. One liter of media collected from a culture of human mesenchymal stem cells (hMSC). The hMSCs were cultured in complete media (CM). The media was centrifuges x 2,465 g, for 15 minutes. The supernatant was collected. The supernatant was subject to a 0.22 filtration. The resulting filtered supernatant was passed over an anion exchange column (Express G). The column was washed with 0.05 M NaCl (20 col. Volume). The column was then eluted with 0.5 M NaCl (2 column). The desired fractions were collected and pooled. FIG. 1b—The collected pooled fractions were dialyzed against PBS. FIG. 1c—EVs were chromatographed on an anion exchange column because the EVs are coated with negatively charged phospholipids.

FIG. 4b—A dramatic increase in vesicles production was demonstrated by culturing MSC under CDPF conditions.

FIG. 5b(ii)—The eluted fraction (left panel) is enriched for vesicles.

FIG. 11a—Exosomes secreted by bone marrow-derived MSCs were first concentrated by elution with 0.5 M NaCl from one anion-exchange column, applied to a second anion-exchange column and eluted step-wise with increasing concentrations of NaCl. FIG. 11b—Total protein in eluted fractions. FIG. 11c—TSG-6 in eluted fractions assayed by ELISA in a capture assay of exosomes. FIG. 11d—Exosomes in eluted fractions as assays by ELISA in which exosomes were first captured with anti-CD63 and detected with anti-CD63.

FIG. 14b(ii)—after incubation in TSG-6 in medium assayed by ELISA. FIG. 14c—(Right panel) shows medium proteins did not bind to a cationic resin. Gels were stained with silver.

FIG. 15a(ii)—(Left panel)—Assays of eluted fractions for protein. FIG. 15a(ii)—(Right panel) Assays of eluted fractions for D63. FIG. 15c(ii)—The three peaks at the lower concentration were 85, 165, and 236 nm. Insets provide photos of nanoparticles in the instrument.

DETAILED DESCRIPTION OF THE PREFERRED EMBODIMENTS

Figure 2:
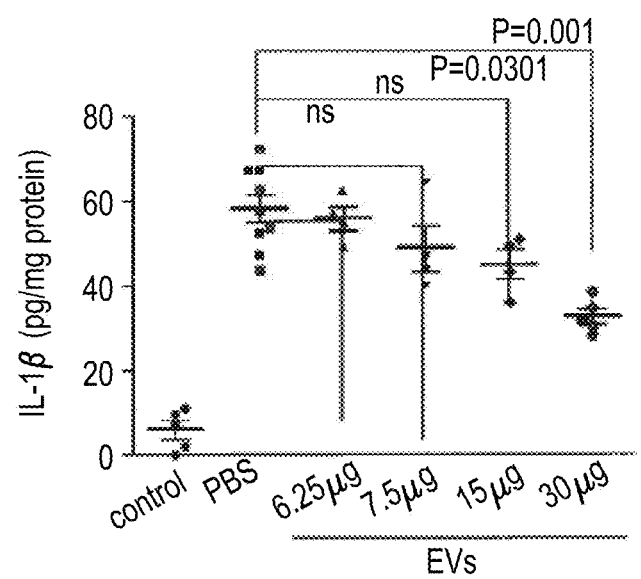
FIG. 2—This figure demonstrates that IV administration of the purified EV preparation reduced brain levels of the pro-inflammatory cytokine IL-1p after traumatic brain injury in mice in a dose dependent manner (doses, 6.25 µg, 7.5 µg, 15 µg, 30 µg).
Figure 3A:
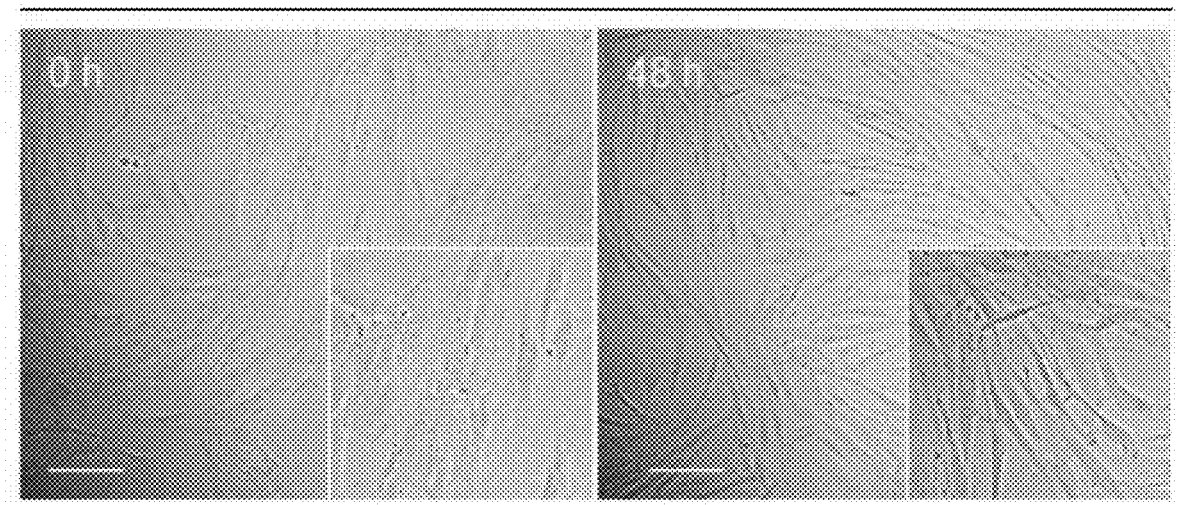
FIG. 3a—hMSCs in CDPF medium are stable.
Figure 3B:
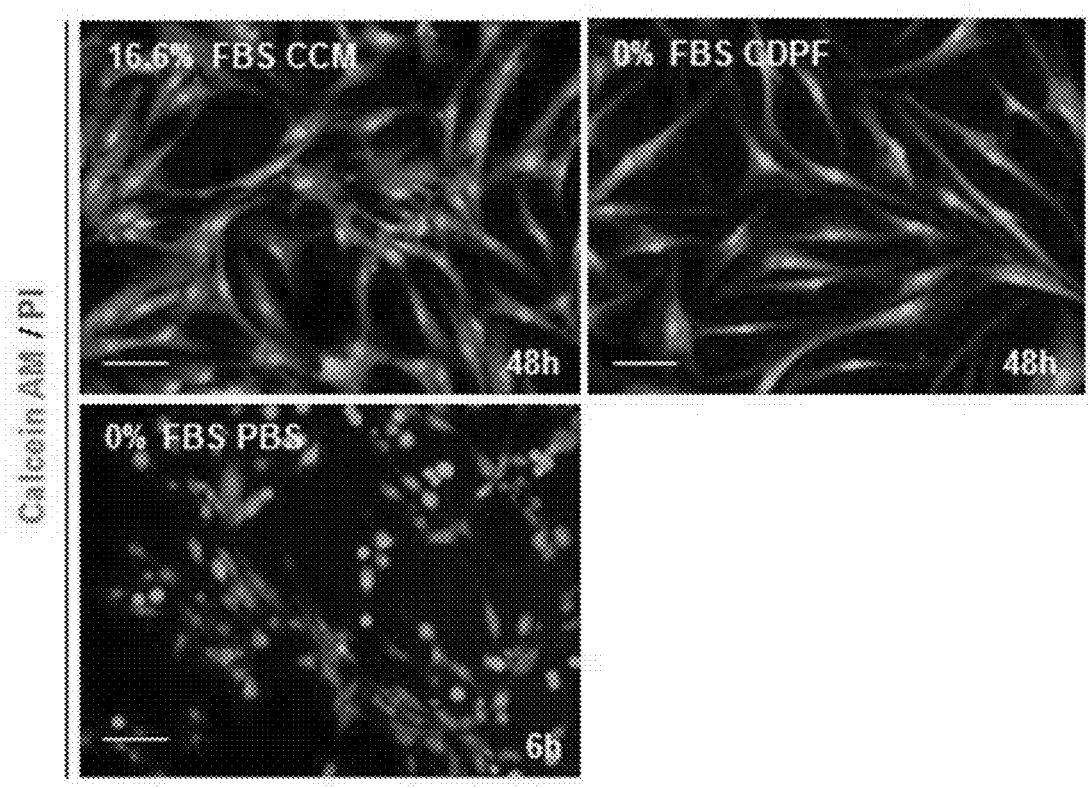
FIG. 3b—hMSCs in CDPF medium do not show major morphological changes.
Figure 3C:
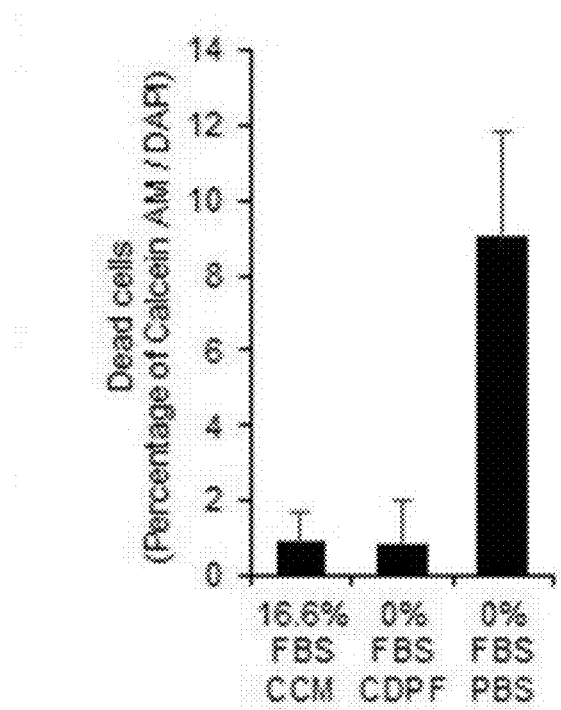
FIG. 3c—hMSCs in CDPF medium show similar survival rate at 48 hr compared to hMSCs in standard medium (CCM) for culture of hMSCs.

Throughout the specification and claims, the following tetras take the meanings explicitly associated herein, unless the context clearly dictates otherwise.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

As used herein, the term "or" is an inclusive "or" operator and is equivalent to the term "and/or" unless the context clearly dictates otherwise.

The term "based on" is not exclusive and allows for being based on additional factors not described, unless the context clearly dictates otherwise.

The term "a," "an," and "the" include plural references. Thus, "a" or "an" or "the" can mean one or more than one. For example, "a" cell and/or extracellular vesicle can mean one cell and/or extracellular vesicle or a plurality of cells and/or extracellular vesicles.

The meaning of "in" includes "in" and "on."

As used herein, "stem cell" refers to a multipotent cell with the potential to differentiate into a variety of other cell types (which perform one or more specific functions), and have the ability to self-renew.

As used herein, "adult stem cells" refer to stem cells that are not embryonic stem cells. By way of example, the adult stem cells include mesenchymal stem cells, also referred to as mesenchymal stromal cells or MSC's.

As used herein, the terms "administering", "introducing", "delivering", "placement" and "transplanting" are used interchangeably and refer to the placement of the extracellular vesicles of the technology into a subject by a method or route that results in at least partial localization of the cells and/or extracellular vesicles at a desired site. The cells and/or extracellular vesicles can be administered by any appropriate route that results in delivery to a desired location in the subject where at least a portion of the cells and/or extracellular vesicles retain their therapeutic capabilities. By way of example, a method of administration includes intravenous administration (i.v.).

As used herein, the term "treating" includes reducing or alleviating at least one adverse effect or symptom of a disease or disorder through introducing in any way a therapeutic composition of the present technology into or onto the body of a subject.

As used herein, "therapeutically effective dose" refers to an amount of a therapeutic agent (e.g., sufficient to bring about a beneficial or desired clinical effect). A dose could be administered in one or multiple administrations (e.g., 2, 3, 4, etc.). However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., cells and/or extracellular vesicles as a pharmaceutically acceptable preparation) for aggressive vs. conventional treatment.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the term "pharmaceutical composition" refers to the combination of an active agent the subcellular vesicles, with, as desired, a carrier, inert or active, making the composition especially suitable for diagnostic or therapeutic use in vitro, in vivo, or ex vivo. As used herein, the terms "pharmaceutically acceptable" or "pharmacologically acceptable" refer to compositions that do not substantially produce adverse reactions, e.g., toxic, allergic, or immunological reactions, when administered to a subject. For example, normal saline is a pharmaceutically acceptable carrier solution.

As used herein, the terms "host", "patient", or "subject" refer to organisms to be treated by the preparations and/or methods of the present technology or to be subject to various tests provided by the technology.

The term "subject" includes animals, preferably mammals, including humans. In some embodiments, the subject is a primate. In other preferred embodiments, the subject is a human.

The following examples are provided to demonstrate and further illustrate certain preferred embodiments and aspects of the present technology, and they are not to be construed as limiting the scope of the technology.

Example 1—Chemically Defined Protein-Free Medium for Mesenchymal Stem Cells

The present example presents the composition of the chemically defined protein free (CDPF) culture medium that is used to culture human mesenchymal stem cells MSCs). The particular supplemental non-protein factors included in the CDPF medium includes a combination of ingredients that has been found by the present inventors to uniquely activate human mesenchymal stem cells in a manner that results in the enhanced production of a population of vesicles not previously observed. These n-EVs of the claimed preparations are negatively charged extracellular vesicles (EVs). This particular population of EVs possesses a surface phospholipid that renders them amendable to a scalable processes of recovery.

The composition of the chemically-defined, protein-free medium in which MSCs are cultured are shown in Table 1:

TABLE 1

CD media for preparation of hMSC-derived micro-vesicles.

| Components | Concentrations (/L) | Sources |
| --- | --- | --- |
| CD-CHO protein-free medium | 925 ml | Invitrogen: 107 43-011 |
| HT* | 10 ml | Invitrogen: 11 067-030 |
| 200 mM L-glutamine | 40 ml | Invitrogen: 25030-081 |
| D-[+]-glucose | 2 g | Sigma: G6152-100g |
| 100x Non-essential amino acid | 10 ml | Invitrogen: 11140-050 |
| 100x MEM vitamin solution | 10 ml | Invitrogen: 11120-052 |

*A mixture of hypoxanthine (10 mM) and thymidine (1.6 mM).

The culture media is free of serum and does not include proteins. This medium is described as a chemically-defined and protein-free medium, and is referenced herein as CDPF medium.

Example 2—Method of Production of hMSC-Derived Extracellular Vesicles from Human hMSC-Cultured Media The present example demonstrates the utility of the present invention for providing a preparation of extracellular vesicles that have been produced from an activated preparation of human mesenchymal stem cells.

Human mesenchymal stem cells prepared from bone marrow (or obtained from human bone) were cultured in the chemically derived protein free medium (CDPF) (Example 1). The hMSCs were activated by incubation in this medium, and produced negatively charged EVs (n-EVs). These negatively charged EVs could then be isolated by anion exchange chromatography.

A frozen vial of about $10^6$ passage 3-4 hMSCs from bone marrow <(medicine.tamhc.edu/irm/mscdistribution.html)> was thawed, and plated at around 500 cells $cm^2$ in 150 mm plates. With 30 mL of complete culture medium (CCM) that consisted of α-MEM, 16.6% FBS, 100 unites/mL penicillin, 100 µg/ml streptomycin and 2 mM L-glutamine. The cultures were incubated for 7 to 9 days until they were 70% confluent. The CCM Medium was replaced every 2 days. The conditions for preparation and culture expansion of the hMSCs have been standardized in Prockop and Reager (2014).

Large Scale Production of EVs from hMSC Cultured Medium.

The cultures in CCM were washed three times with PBS, and all CCM removed. The human mesenchymal stem cells were then cultured in CDPF medium (protein-free, serum-free) (see Example 1). After 6 hour culture in CDPF medium, the CDPF medium was changed to fresh CDPF medium, and further cultured for 42 hours.

After 42 hours, the CDFM medium, now termed conditioned CDFM from the release of materials from the hMSCs into the media, was collected and centrifuged at 2,465×g, 15 minutes, to remove any cells and debrie. The conditioned CDFM media was then applied onto an anion exchange column, and the column was eluted with 500 mM NaCL. The eluted fractions were collected. Selected eluted fractions were then concentrated using centrifugal filtration, and the negatively charged extracellular vesicles (n-EVs) present in the eluted fractions were obtained. Doses of n-EVs: 3.8 µg, 7.5 µg, 15 µg, 30 µg, in sterile saline.

The method provides for a scalable process having greater efficiencies of production, as well as greater uniformity and constancy of n-EVs provided in the preparations.

Example 3—Characterization of Extracellular Vesicles

The present example provides a description of the EVs provided according to the present scalable production methods.

The n-EVs of the present invention are highly anionic, and can be isolated on an anionic exchange column.

The enriched populations of n-EVs may be distinguished from other vesicle preparations by reference to several characteristics. For example, the detectable surface epitopic characteristics of the preparations may be described as CD63+ and CD81+, and/or as being absent detectable surface levels of (i.e., are negative for) CD9, and any combination of two (2) or more, or all, of the surface epitopes CD 29, CD44, CD49c, CD50, CD59, CD90, CD105, CD147, CD166, and HLA-1ABC. Of note, these epitopes CD 29, CD44, CD49c, CD50, CD59, CD90, CD105, CD147, CD166, and HLA-1ABC, are present on the surface of the mesenchymal stem cells that produce a population of extracellular vesicles that are ultimately formulated in the preparations of n-EVs of the present invention.

In addition, the n-EV preparations, as well as the compositions that contain them, are suitable for use in humans. They may be formulated as part of an injectable preparation, or other form, so as to provide a pharmaceutically acceptable preparation. Thus, as part of an injectable preparation, the n-EVs may be formulated in a pharmaceutically acceptable carrier solution, such as saline.

Alternatively, the n-EVs may be contained in a biologically compatible drug delivery depot, such as a depot that may be surgically implanted into a patient. The depot would permit the n-EVs to be delivered into the system of the patient, thus providing the intended therapeutic effect.

The n-EV preparations may also be described as a human n-EV preparation, as they are prepared from human mesenchymal stem cells, obtained from a human tissue source, such as bone marrow.

Example 4—Administration of n-EV Preparations Reduces Traumatic Brain Injury Damage In Vivo The present example demonstrates the utility of the present invention to reduce inflammation. In particular, the present example demonstrates the utility of the present invention as a therapeutic method for reducing inflammation of the brain. Inflammation of the brain typically results, for example, as a result of traumatic brain injury.

A mouse model for traumatic brain injury was used in the present example. In particular, mice having a controlled cortical contusion were used.

i.v. Injection of n-EVs into Mice: Doses of n-EVs: 3.8 µg, 7.5 µg, 15 µg, 30 µg in sterile saline 30 µg of n-EVs (CM-Q fractions) was injected via tail vein after TBI (controlled cortical contusion). The brain tissue of the animal was then collected 12 hours after the injection, and IL-1β levels were measured by ELISA.

The results are shown in FIGS. 3, 4, 5 and 6. The data demonstrates that intravenous injection of 30 ug of the nEV preparations significantly reduced inflammation in an animal suffering from traumatic brain injury, as reflected in reduced levels of IL-1β levels 9p<0.001) in brain tissue harvested from the treated animals.

Example 5—In Vivo Treatment with nEVs Reduces Inflammatory Response and Improves Cognitive Ability after Traumatic Brain Injury; Response to n-EVs is Dose Dependent The present example demonstrates the utility of the present invention for providing a pharmaceutical preparation suitable for injection in vivo for reducing brain inflammatory response to traumatic brain injury. In addition, the present example demonstrates the utility of the invention for providing a treatment useful for improving cognitive abilities in an animal having suffered traumatic brain injury.

Traumatic brain injuries (TBI), defined here to include mild Balms of TBI injury such as concussion, produce both direct and a secondary inflammatory response that prolongs and increases the injury. In addition, a major consequence of TBI is cognitive and behavioral defects that can be long lasting. However, the development of effective drugs for the therapy of TBI is demonstrated using the nEVs of the present invention.

A pharmaceutically acceptable preparation of nEVs of the present invention were prepared as described in Example 4.

Materials and Methods.

1. Preparation of Concentrated Conditioned Medium.

Vials of human MSCs derived from human bone were plated at 500 cells $cm^2$ in 150 mm plates, and cultured in 30 mL of complete culture medium (CCM) that consisted of α-MEM, 16.6% FBS, 100 unites/mL penicillin, 100 µg/ml streptomycin and 2 mM L-glutamine. The cultures were incubated for 7 to 9 days until they were 70%-80% confluent. The CCM Medium was replaced every 2 days.

The cultures in CCM were washed three times with PBS, and all CCM removed. The human mesenchymal stem cells were then cultured in CDPF medium (protein-free, serum-free) (see Example 1). After 6 hour culture in CDPF medium, the CDPF medium was changed to fresh CDPF medium, and further cultured for 42 hours. After 42 hours, the CDFM medium, now termed conditioned CDFM (containing material/factors released and/or secreted from the hMSCs into the media), was collected and centrifuged at 2,465×g, 15 minutes (or 2,500×g, 15 min), to remove any cells and debris.

Figure 4A:
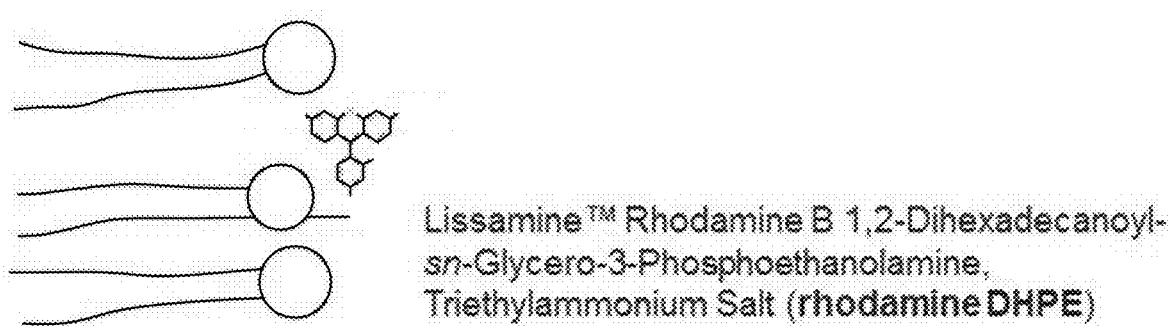
FIG. 4a—hMSCs actively produce vesicles under CDPF medium culture conditions.
Figure 4A:
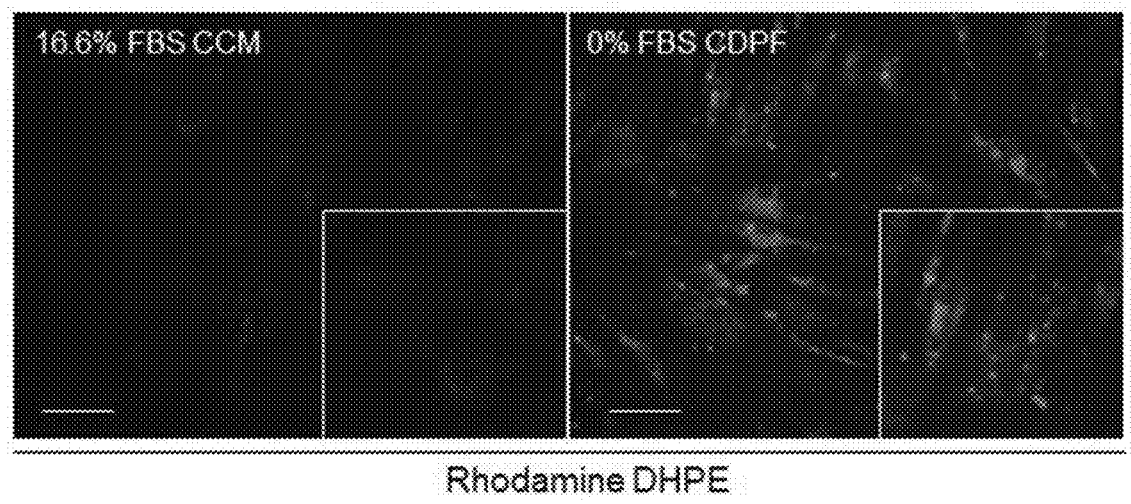
Figure 4B:
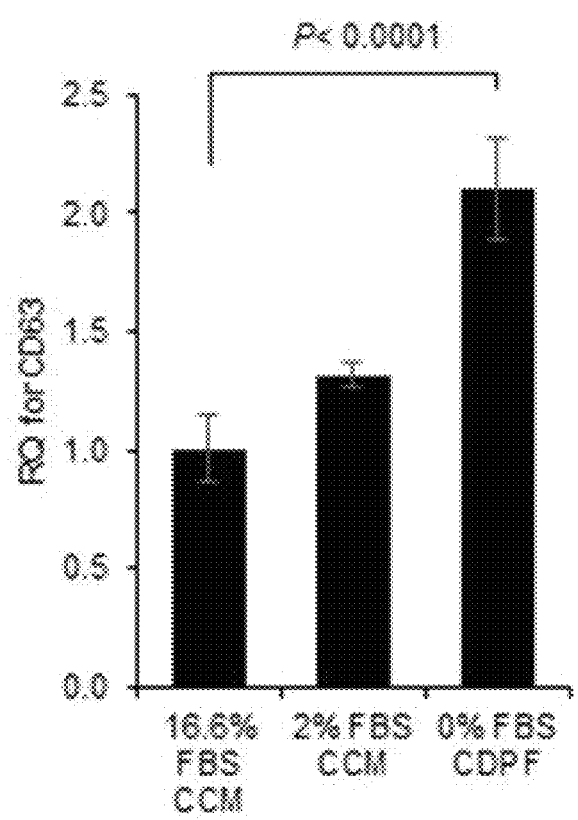
Figure 4C:
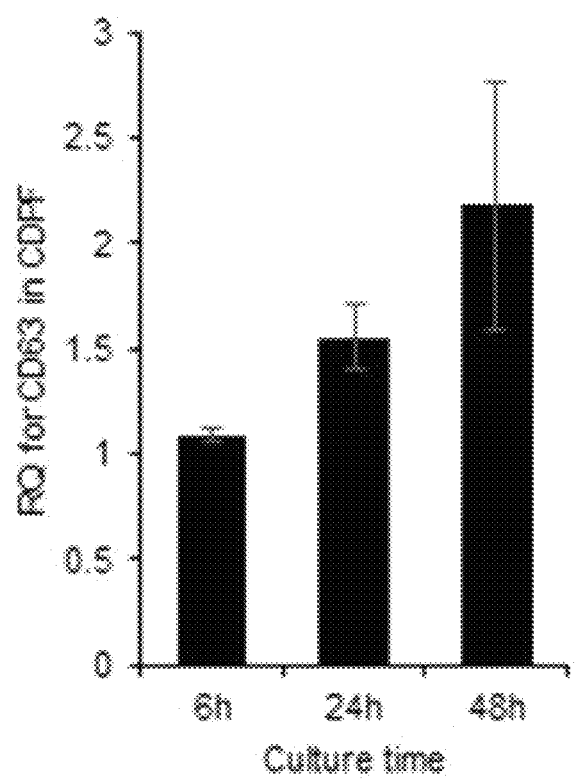
FIG. 4c—nEv production in CDPF culture conditions for 6 hr, 24 hr and 48 hours.
Figure 4D:
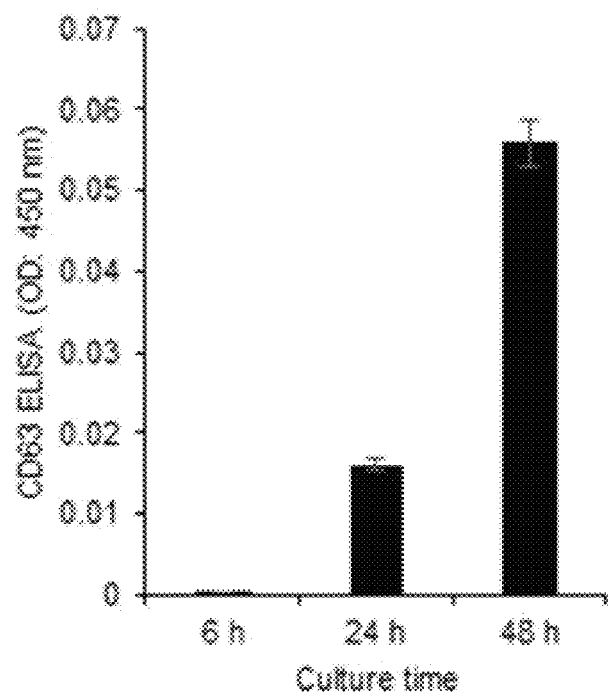
FIG. 4d—CD63 expressed in CDPF media in a time dependent manner FIG. 4e—Silver stain analysis demonstrating hMSCs in CDPF medium express the pro-inflammatory cytokine (IL-1β) and the anti-apoptosis (STC-1) and anti-inflammatory (TSG-6) proteins in a time-dependent manner (0 hr, 2 hr, 6 hr, 24 hr).
Figure 4E:
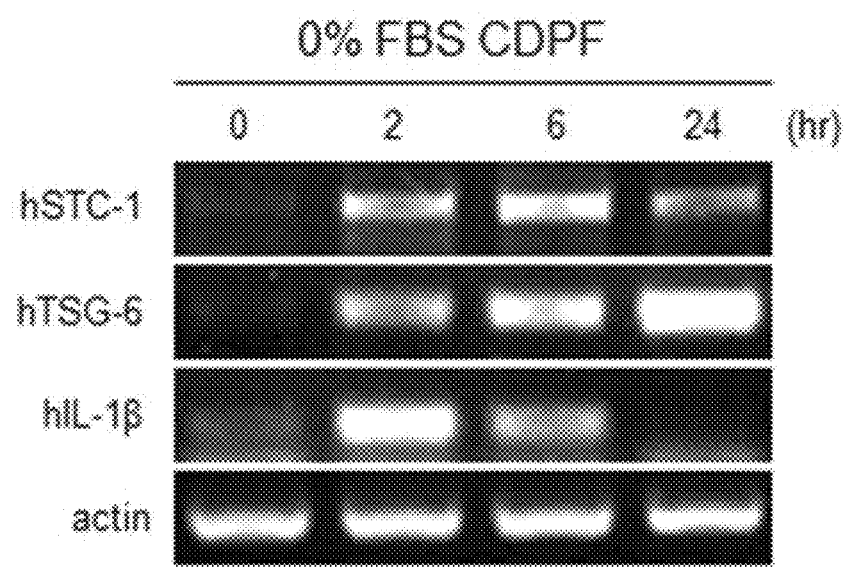
Figure 4F:
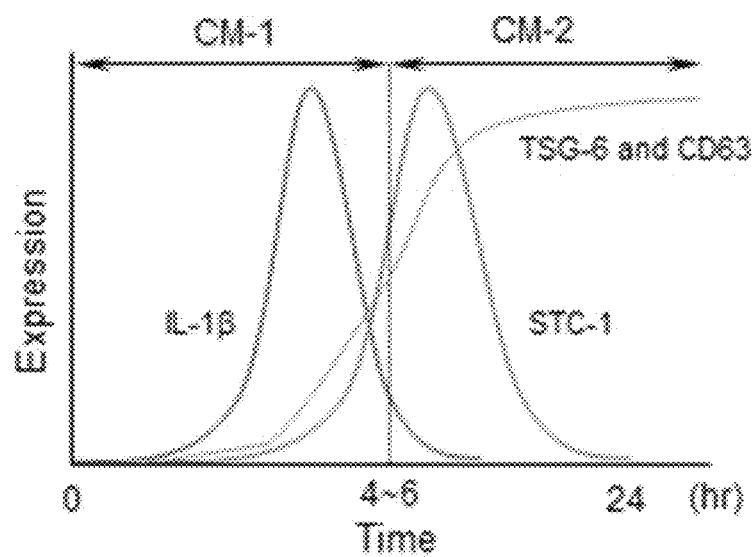
FIG. 4f—graph representation of IL-43, STC-1 and TSG-6 protein production at 0, 4-6, and 24 hours.
Figure 5A:
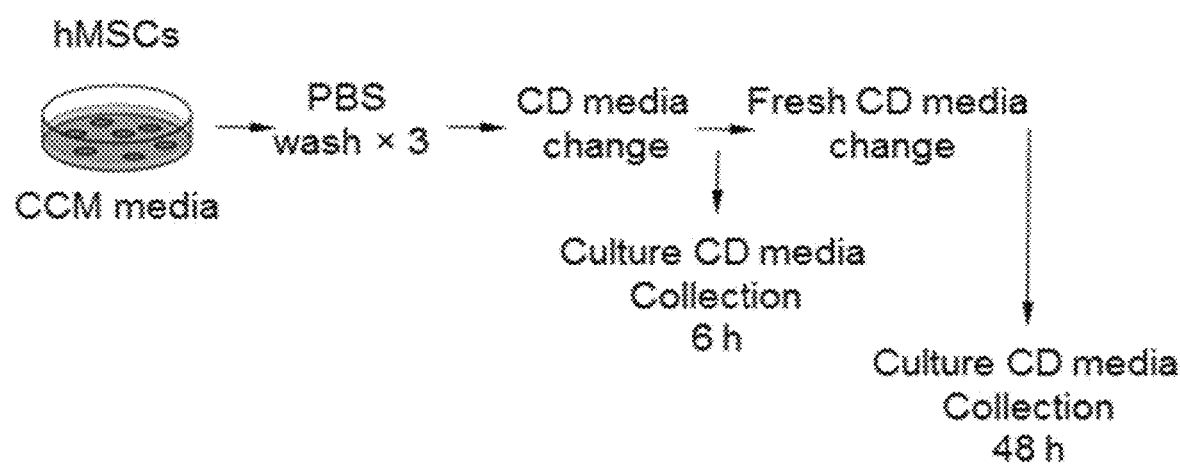
FIG. 5a—Isolation of n-EVs enriched fractions by an anion exchanger column. Schematic outline shows the collection of medium from hMSCs in cultured CDPF.
Figure 5B:
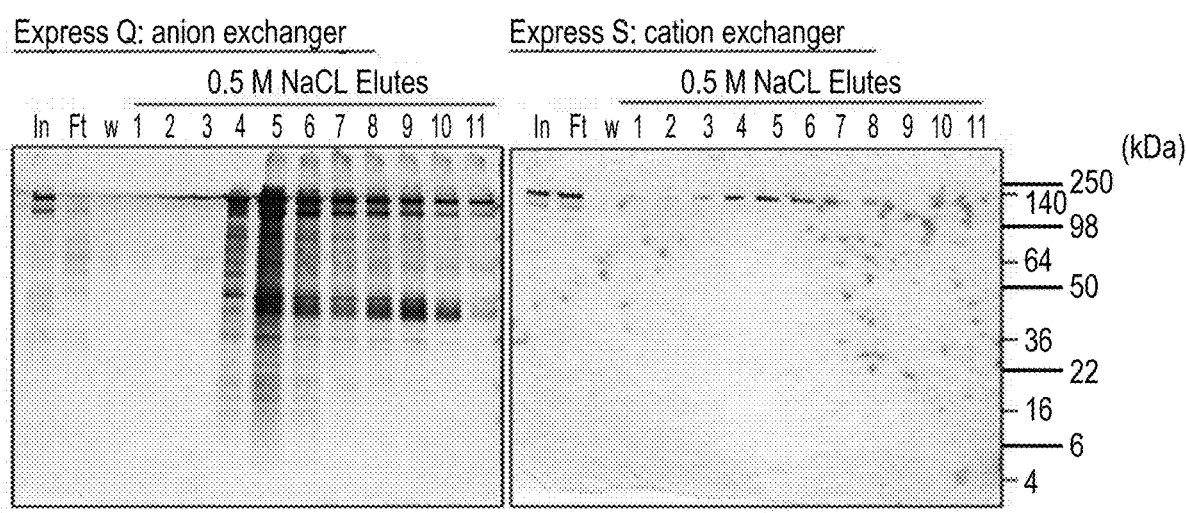
FIG. 5b(i)—Most of the media components bound to the anion exchanger resin (left panel), but not to a cation exchange resin (right panel).
Figure 5B:
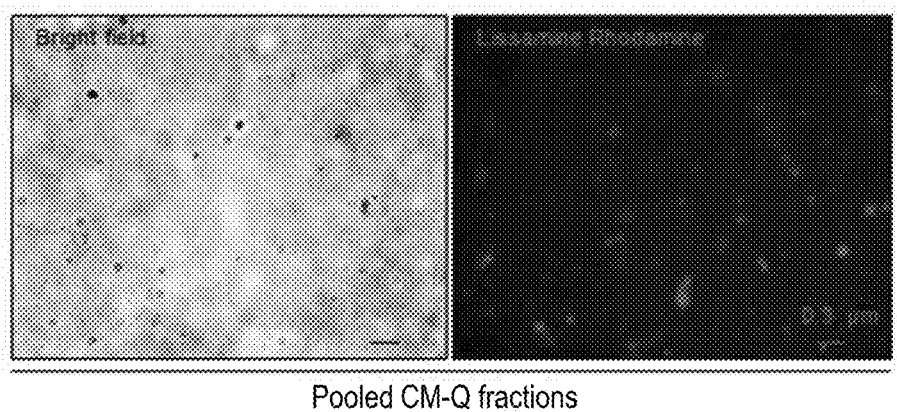
Figure 5C:
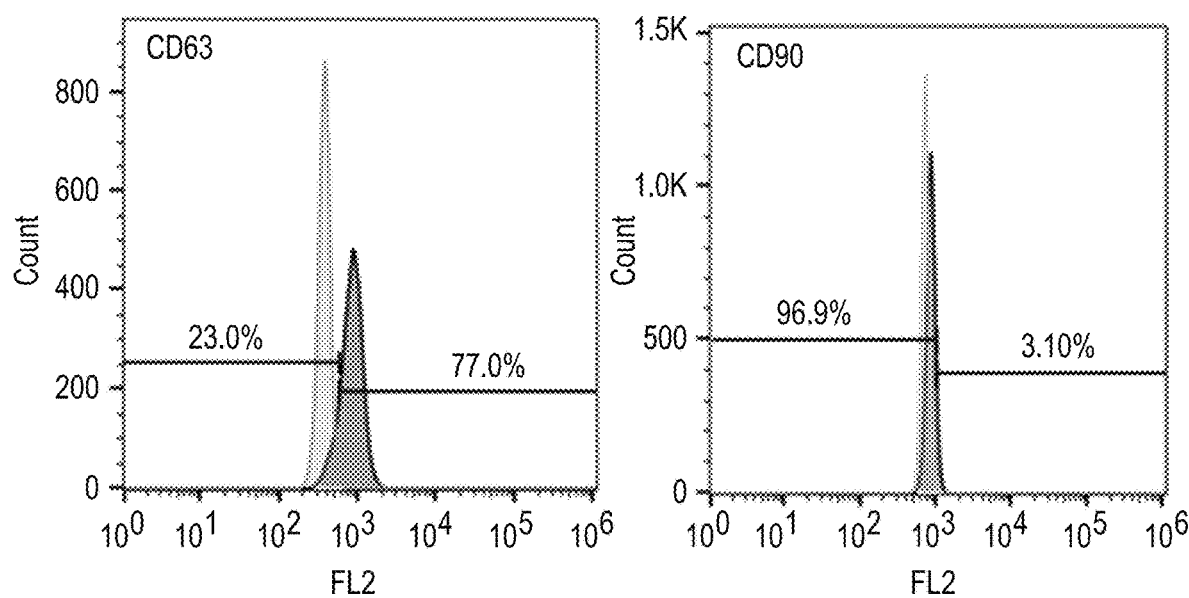
FIG. 5c—The vesicles are enriched for CD63, an epitope characteristic of exosomes (left panel), and negative for CD105, an epitope found on hMSCs (right panel).
Figure 6A:
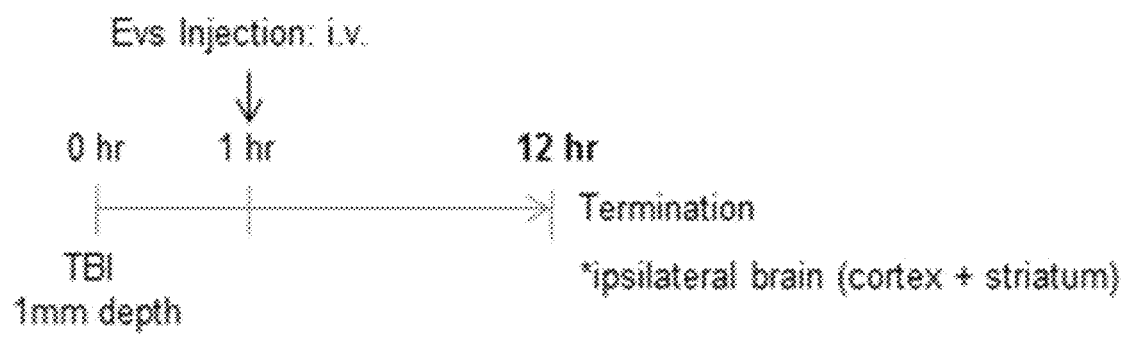
FIG. 6a—Chromatographically isolated n-EVs reduced the expression of the pro-inflammatory cytokine IL-1β in ipsilateral brain, the time line of the in vivo experiment.
Figure 6B:
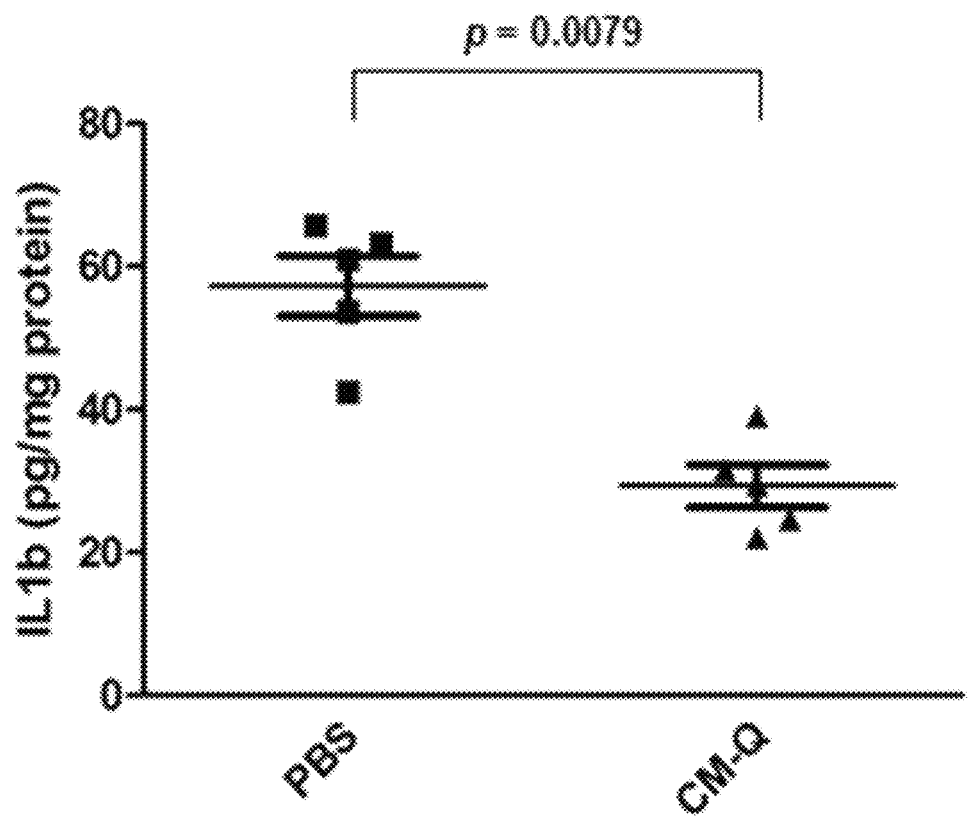
FIG. 6b—Injection of n-EVs significantly decreases the expression level of IL-1β in damaged brain area.

The conditioned CDFM media was then applied to an anion exchange column, and fractions collected from the column, being eluted with 500 mM (0.5 m) NaCL. The eluted fractions were collected. Selected eluted fractions were then concentrated using centrifugal filtration, and the negatively charged extracellular vesicles (n-EVs) present in the eluted fractions were obtained. This single broad peak collected was determined to contain CD63 (FIG. 4*d*, FIG. 5*c*).

2. Controlled Cortical Impact Injury.

Mice (CD57BL/6J) were anesthetized, and 4 mm craniotomy was performed on the right cranial vault. The center of the craniotomy was placed at the midpoint between bregma and lamda. Animals received a single impact (depth 1.0 mm, velocity 4.5 m/sec, dwell time 250 ms). Chromatographically isolated nEVs were injected via the tail vein. at 1 hour after TBI at a dose of 3.8, 7.5, 15 and 30 μg per mouse.

3. Assessment.

Brain Inflammation: (IL-1β, IL-6, and TNF-α)

To measure cytokine levels, mice were anesthetized and transcardially perfused with 0.9% saline. The injured cortex and hippocampus were collected. The protein was extracted from the tissue and the levels of cytokines (IL-1β, IL-6, and TNF-α) were determined using R&D Quantikine® ELISA kit.

To investigate which cells produce IL-1β, mice were anesthetized and transcardially perfused with 0.9% saline and 4% parafoimaldehyde in PBS. The brain was cut at 50 intervals and stained with primary antibody against GFAP and IL-1β.

2. Behavioral Test.

To assess cognitive deficits, Morris water maze test and pattern separation test were conducted on 28-35 days after TBI.

Figure 7A:
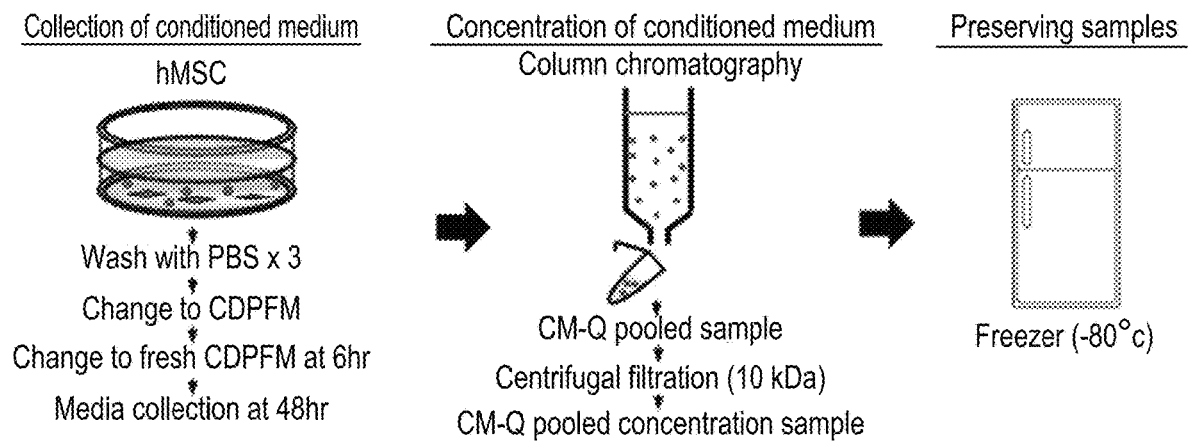
FIG. 7a—Method for preparation of MSC derived n-EVs. The schematic depiction of the isolation protocol of n-EVs.
Figure 7B:
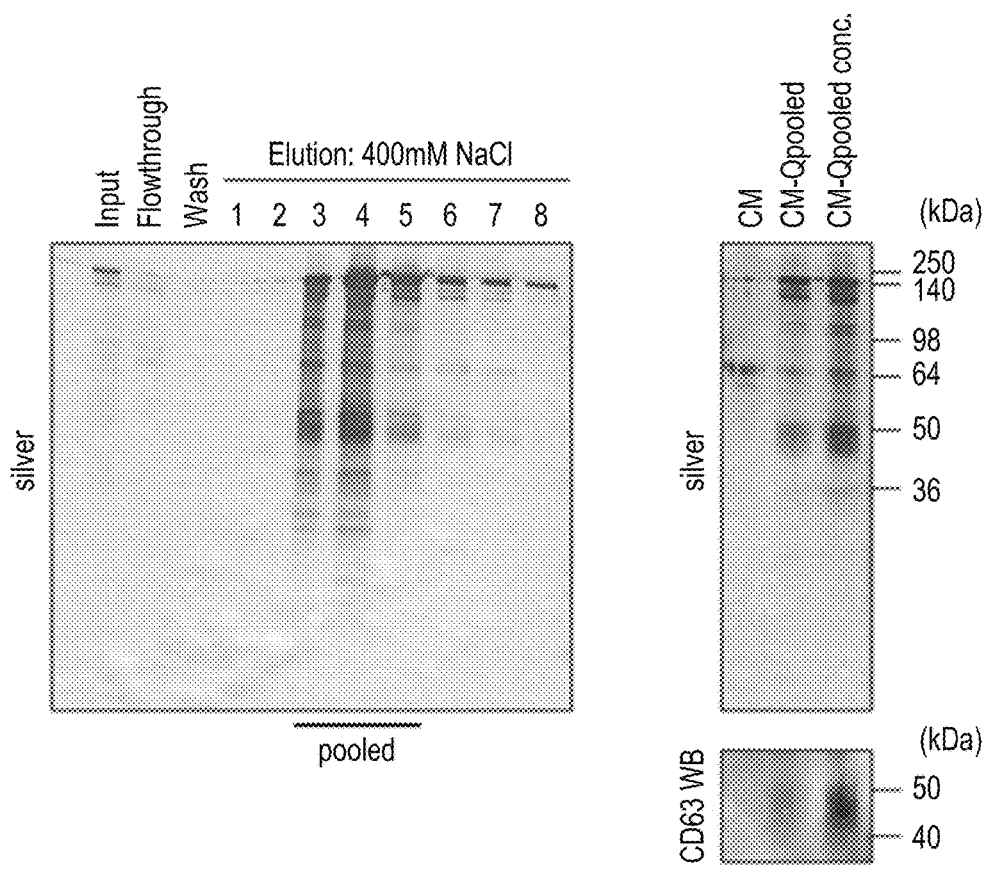
FIG. 7b—The eluted fractions, E1 to E8, were collected and an equal volume of E1 to E8 were separated by SDS PAGE and stained silver. The peak fractions were pooled (CM-Q pooled). CM-pooled was concentrated using Amicon® ultra centrifugal filters (CM-Q pooled concentration). The samples were analyzed for the presence of proteins by silver staining and CD63 with Western blots.
Figure 8A:
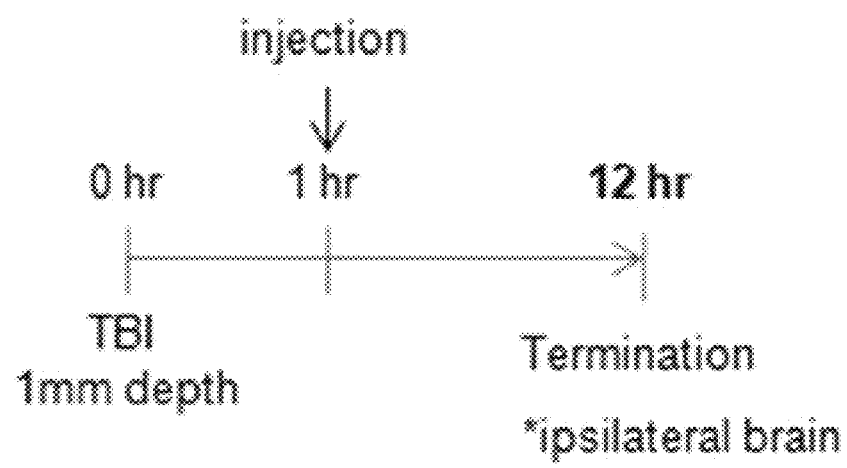
FIG. 8a—Chromatographically isolated n-EVs reduced IL-1β expression in brain in a dose dependent manner. A schematic showing the time line of experiments with TBI and exosomes. Mice were injected intravenously with n-EVs (3.8, 7.5, 15, 30 µg protein/mouse) 1 hr after TBI and the brain was collected at 12 hours.
Figure 8B:
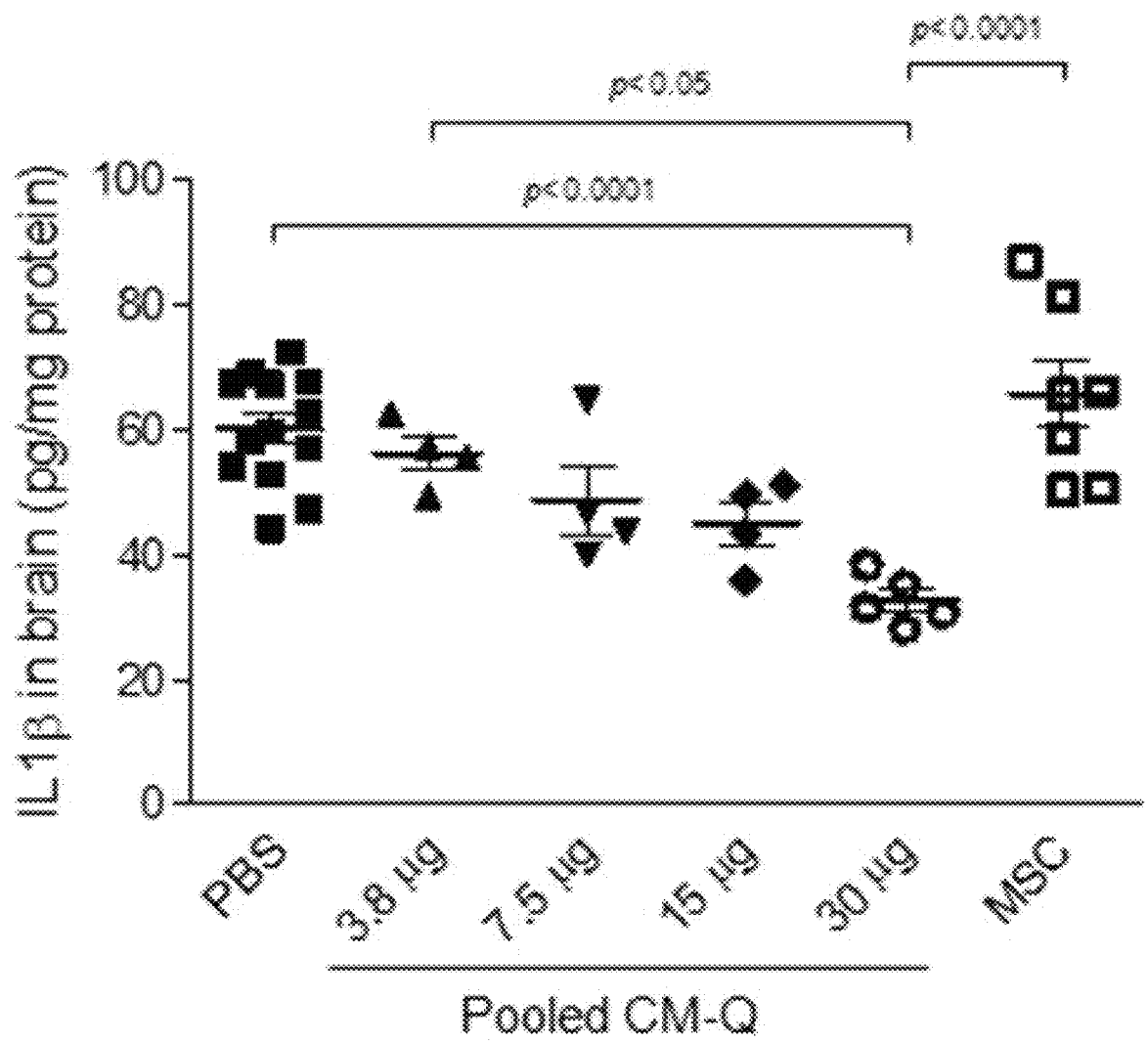
FIG. 8b—IL-1β measurements.
Figure 8C:
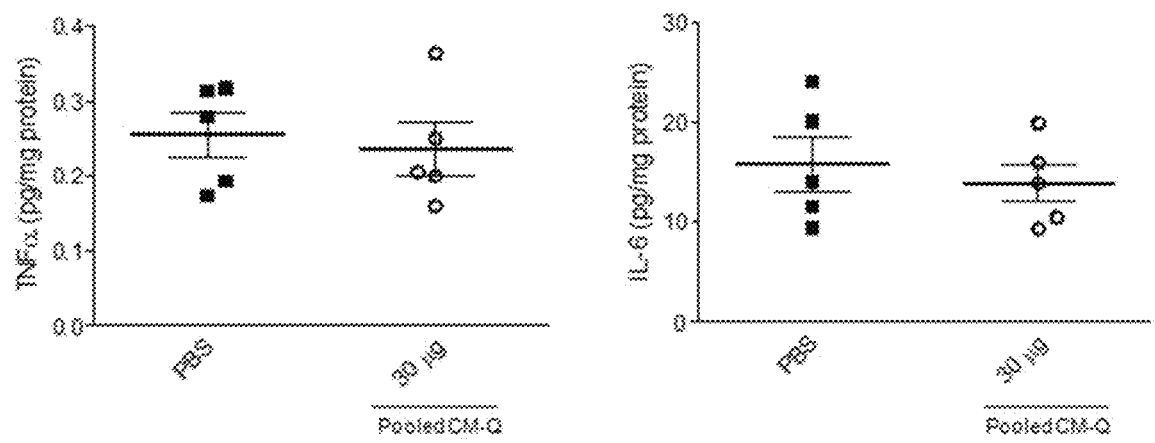
FIG. 8c—TNF-α and IL-6 measurements using R&D Quantikine® kit. Bars represent mean±SEM.
Figure 9A:
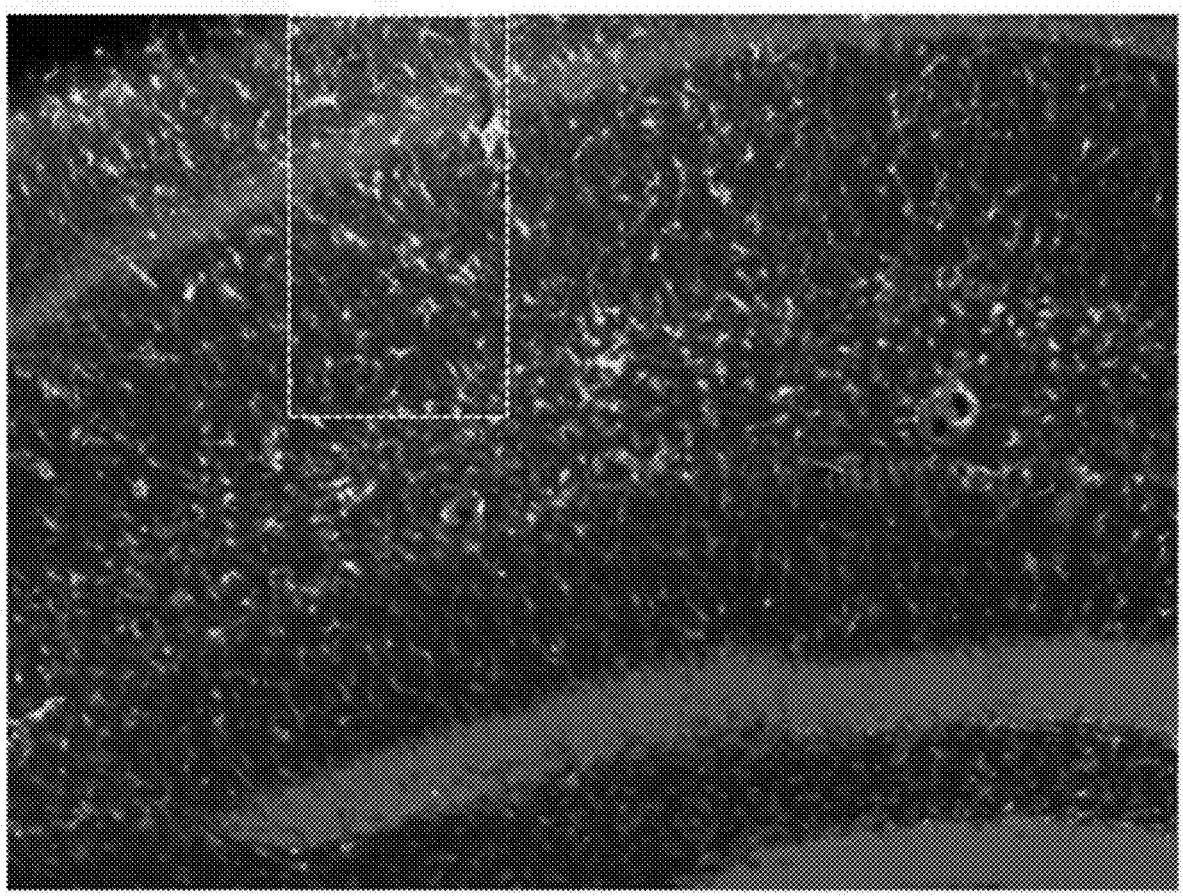
FIG. 9a—IL-1β expression by astrocytes in hippocampus after TBI.
Figure 9B:
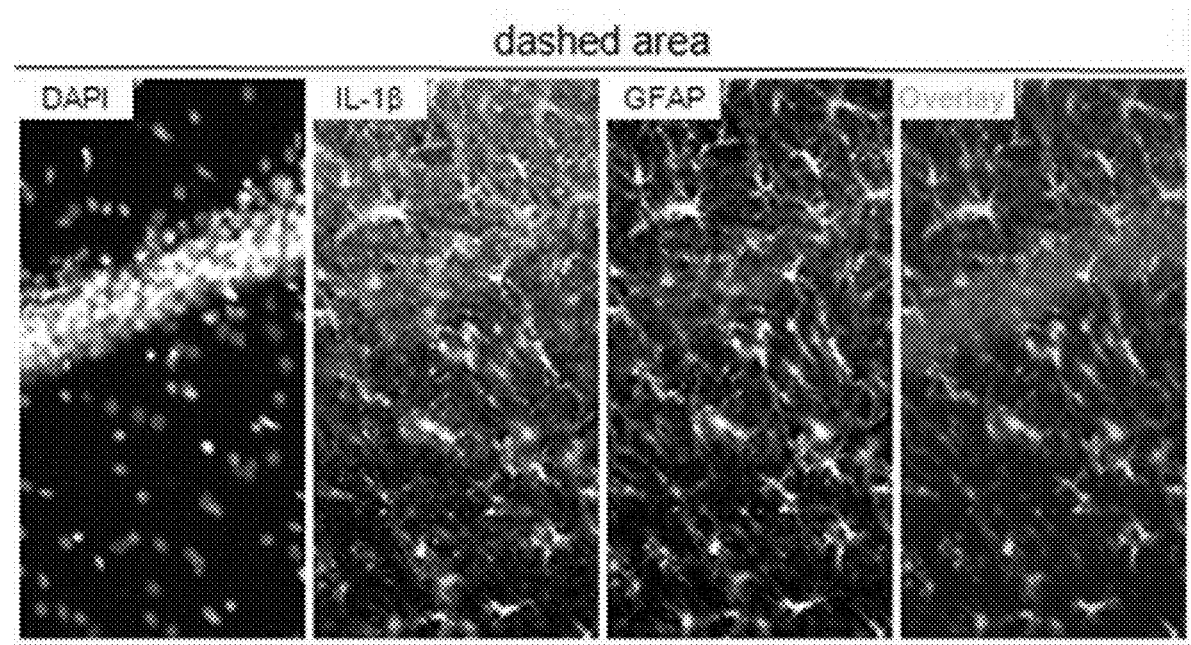
FIG. 9b—The hippocampus tissue sections were stained with DAPI (blue), IL-1β (red), and GFAP (green).

The results obtained in this study are depicted at FIGS. 7, 8, and 9.

As shown in FIG. 9, administration of the n-EVs reduced neuroinflammation in the brain, as demonstrated chromatographically in the IL-1β expression levels observed in the ipsilateral brain of TBI animals. The reduction in inflammation is shown to be dose dependent, with the greatest reduction in brain IL-1β being demonstrated at the 30 μg dose of n-EV preparation.

Figure 10A:
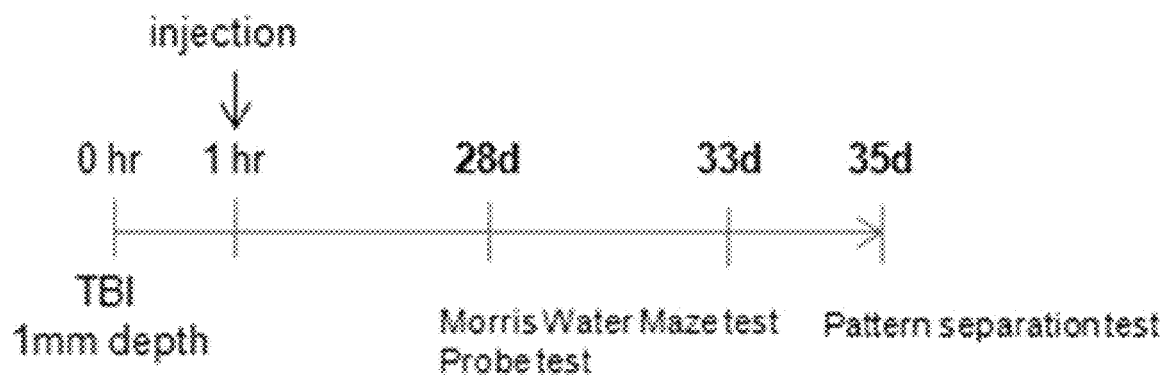
FIG. 10a—Chromatographically isolated n-EVs improve memory function; A schematic showing the timeline of experiments of behavior tests.
Figure 10B:
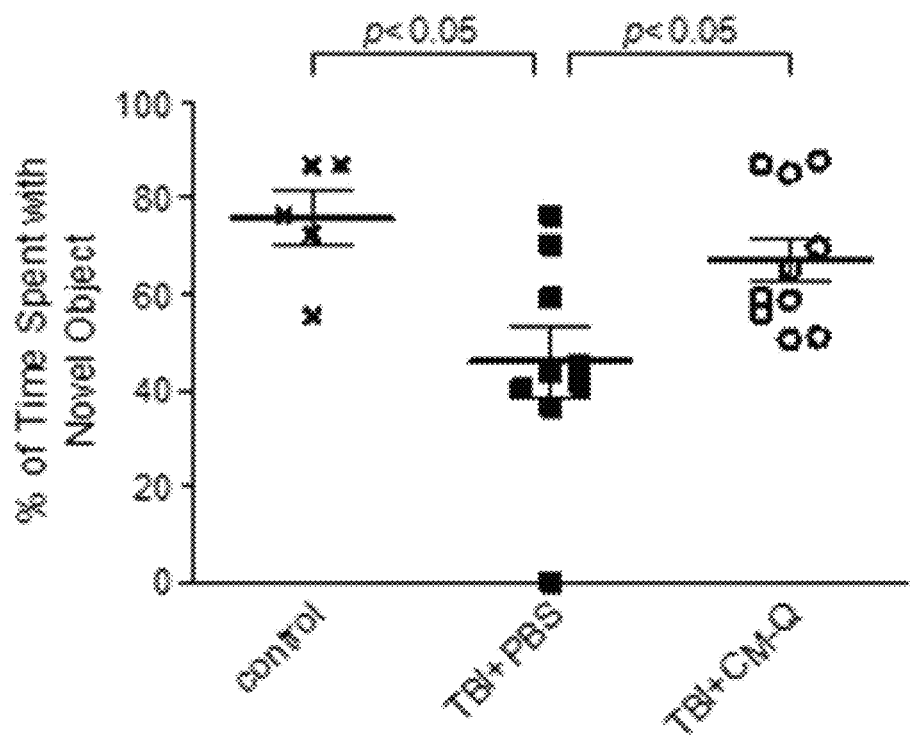
FIG. 10b—Pattern separation test was assessed at 35 days after TBI. Dot charts compare the percentage of time spent between the familiar object and the novel objects in naive-mice and TBI-mice with or without n-EVs treatment.

As shown in FIG. 10*b*, (Pattern separation test assessed at 35 days after TBI), the percentage of time spent between the familiar object and the novel objects in naive-mice and TBI-mice with n-EV treatment was less than the time spent by TBI mice without n-EVs treatment.

Figure 10C:
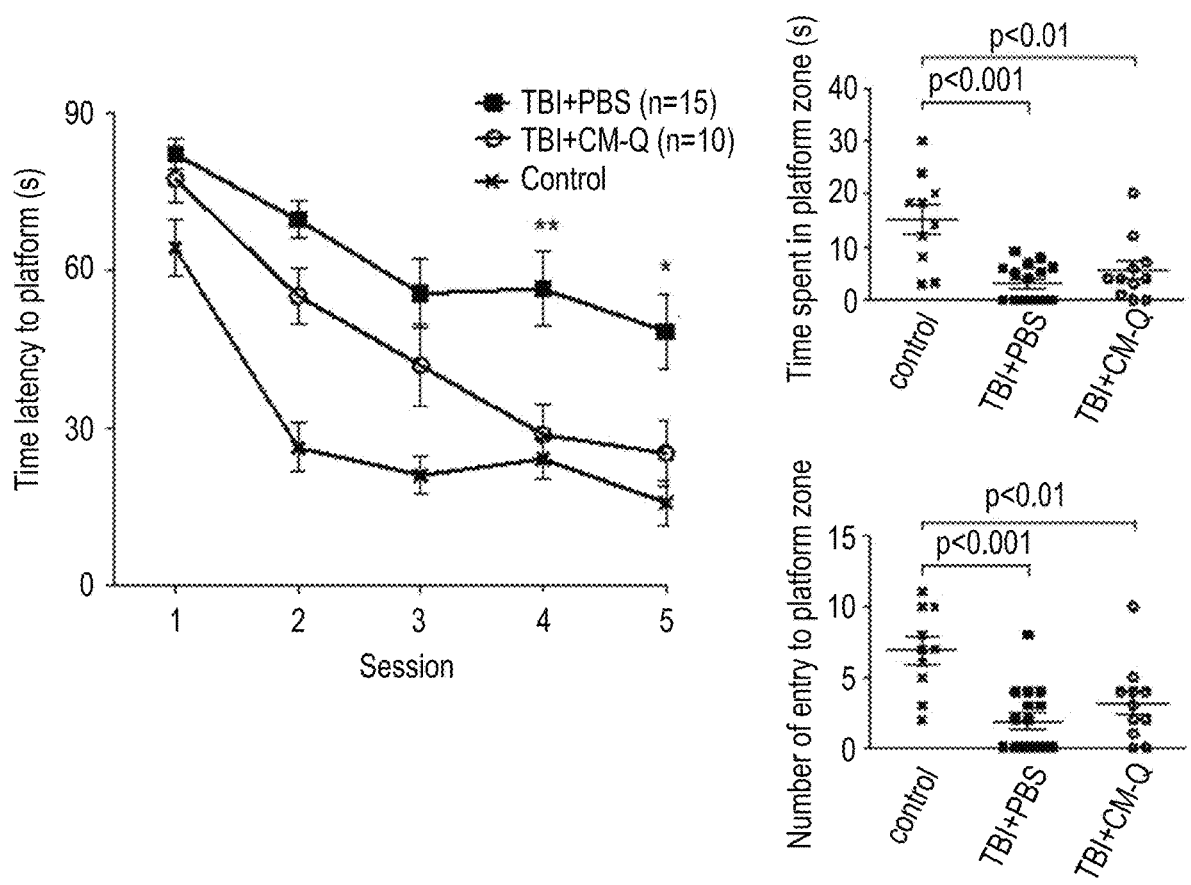
FIG. 10c—The Morris water maze test was assessed on 28-31 days after TBI and therapy with n-EVs. Probe tests (memory retrieval) tests were performed at 24 hr after the last learning session. Values were mean±SEM. *p<0.05; **p<0.01.

FIG. 10*c* provides the results observed with the TBI animals using the Morris water maze test. This test was assessed on 28-31 days after TBI and therapy with n-EVs. Performance in the test was improved in TBI animals receiving the n-EV treatment, while performance in animals not receiving the n-EV treatment was poor.

Probe tests (memory retrieval) tests were performed at 24 hr after the last learning session. (mean±SEM. *$p<0.05$; **$p<0.01$.). As shown, memory function was shown to be improved in TBI animals that received n-EV compared to TBI animals that did not receive the n-EV treatment.

Example 6—Use of n-EV Containing Pharmaceutical Preparations

The present example demonstrates the utility of the present preparations as a pharmaceutically acceptable preparation useful for the treatment of numerous human diseases, including arthritis, inflammation, hearing loss, cancer (colon, breast, liver, ovarian, prostate, etc.), stroke, kidney failure, diabetes, Parkinson's Disease, myocardial infarction, multiple sclerosis, graft versus host disease, Alzheimer's Disease, dementia, brain injury, cognitive disorders, bone loss (osteoporosis), loss of memory, and the like. The present n-EV enriched preparations may also be utilized to reduce a patient's risk of suffering from these conditions, as the preparation may be administered to a patient before presenting with the pathology.

The above conditions have been treated with other types of formulations. However, it is anticipated that the specific n-EV enriched preparations provided here with illicit an enhanced response. In addition, using the present approach, a patient will not be exposed to the application of a live cell culture, such as a prepared stem cell culture. The administration of any preparation that contains living cells, such as a live preparation of replicating mesenchymal stem cells, suffers from many disadvantages, including the unpredictability of how the preparation will interact with a patient's own system, and the duration of any therapeutic effect. The injection/administration of a stem cell preparation also lacks any criteria to measure the amount of active agent being delivered to a patient, or to standardize the active pharmaceutical ingredient (API) contained in a preparation being administered.

Upon a human patient presenting with one or more of the above noted pathologies, or who is at risk of suffering from one or more of the above pathologies, a pharmaceutically acceptable preparation comprising an enriched population of n-EVs may be provided. The attending clinician will determine the particular dose and dosing regimen to be given to the patient, based on the appropriate standard of care and the specific condition of the individual patient.

The dose levels identified for in vivo use of the n-EV preparations in animals (3.8 μg, 7.5 μg, 15 μg, 30 μg, in sterile saline), may be used to calculate an appropriate dose for a human patient, based on, among other things, weight, age, height, sex, relative health status, presenting pathologies, and the like. Recognized as a definitive reference on the science and practice of pharmacy, Remington: The Science and Practice of Pharmacy ($22^{nd}$ edition), (incorporated herein in it's entirely), may be used and followed creating and/or modifying the pharmaceutical formulation and dosage preparation suitable for the specific human patient being treated.

Subsequent doses may be administered to a patient, depending in part on the patient's response or lack of response. The response of a patient for a particular treatment with an n-EV containing preparation may also be monitored by monitoring of biologically active molecules in the patient's blood, urine or other fluid. For example, in the treatment of diabetes, a patient's blood may be measured to determine the level of insulin in a blood sample after administration of a dose of the n-EV containing preparation.

In the use of the present n-EVs in the treatment of inflammatory disease (such as arthritis, etc.), a patient's blood sample may be measured for a pro-inflammatory cytokine, such as IL-Ip. Alternatively, or in addition, the anti-apoptosis protein, STC-1, and the anti-inflammatory protein, TSG-6, may be measured in a patient sample as a mechanism to determine the patient's response, as well as to define an end-point for treatment.

Example 7—Chromatographic Isolation of Two Distinct Kinds of Exosomes

Exosomes secreted by bone marrow-derived MSCs eluted as a single peak from an anion-exchange column. Upon re-chromatograph of this single peak from the first column through a second anion-exchange column, and eluting this second column under different conditions, two distinct peaks are identified.

Figure 11E:
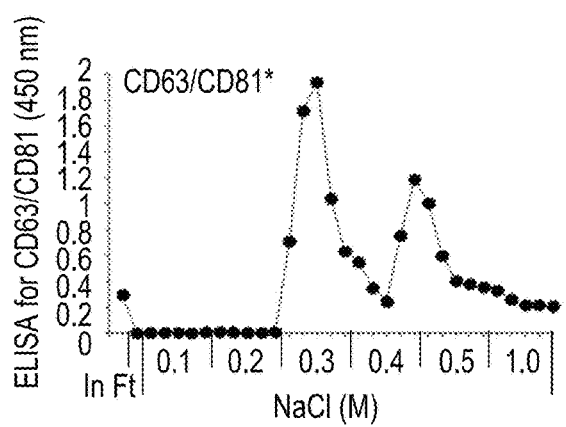
FIG. 11e—Similar assay of fraction in which exosomes were captured with anti-CD63 and detected with anti-CD81.
Figure 11F:
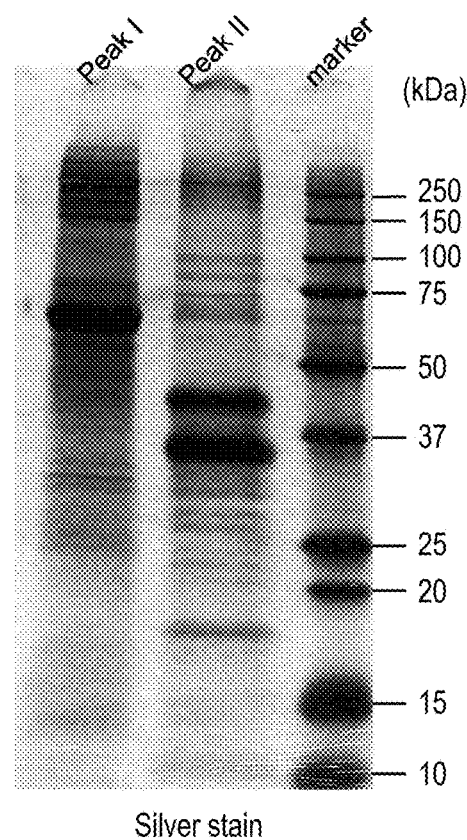
FIG. 11f—Assay of proteins in the two peaks by SDS-polyacrylamide electrophoresis demonstrating marked differences in protein content.

FIG. 11 demonstrates that the exosomes eluted from this process, a process that included a second anion exchange column run, provided fractions of exosomes that eluted at two distinct peaks from the second column. Assay of the two peaks demonstrated that they contained exosomes of the same size. Analysis of the proteins in the two peaks by SDS-polyacrylamide gel electrophoresis demonstrated that the protein contents of the vesicles in the two peaks were very different. Therefore the exosomes in the two peaks are likely to contain distinctly different therapeutic factors. In a first of these identifiable peaks, the eluted fractions contained a higher concentration of higher molecular weight proteins, while in the second of these identifiable peaks, a higher concentration of the lower molecular weight proteins is identified.

Example 8—Efficacy of Intranasal Administration of Extracellular Vesicles for Restraining Status Epilepticus Induced Neuroinflammation Multiple conditions including head trauma, stroke and Alzheimer's Disease can trigger status epilepticus (SE). Hippocampus is highly susceptible to SE where a cascade of morphological and functional changes referred to as epileptogenesis occur over weeks and months after SE and cause temporal lobe epilepsy (TLE), typified by spontaneous recurrent seizures (SRS), and cognitive and mood dysfunction associated with declined neurogenesis. In the realm of SRS occurring in the chronic phase after SE, early changes such as increased oxidative stress, inflammation characterized by reactive astrocytes and activated microglia, abnormal neurogenesis, and loss of subclasses of gamma-amino butyric acid positive interneurons have received great interest. Antiepileptic drug (AED) therapy can stop SE in most instances but cannot adequately suppress SE-induced detrimental changes listed above. Hence, an ideal therapeutic strategy for SE should be capable of restraining oxidative stress, inflammation, aberrant neurogenesis and neuron loss.

Figure 12A:
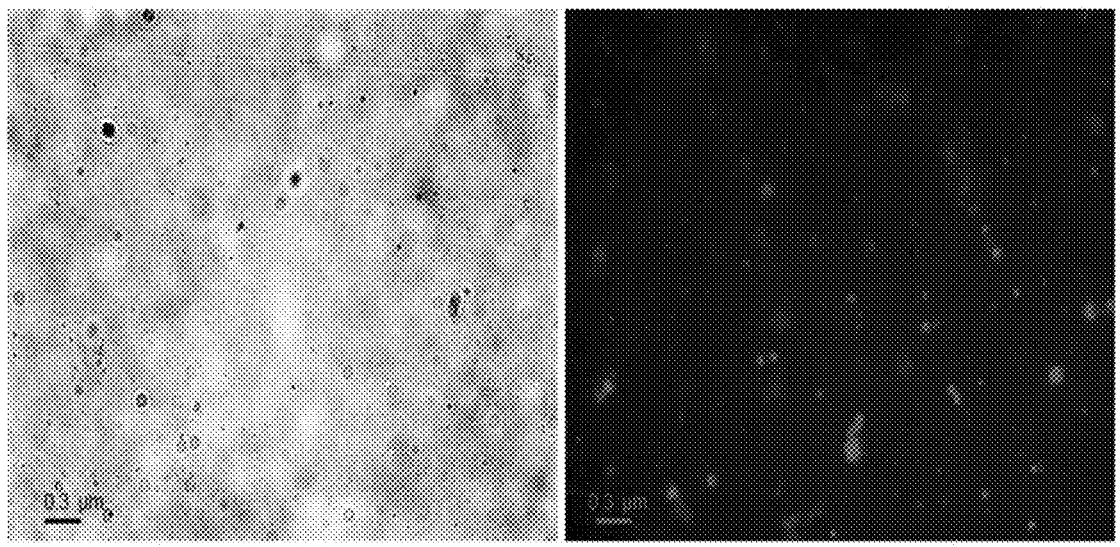
FIG. 12a—Production of EVs (exosomes) containing expressed protein by induced pluripotent stem-derived bone marrow MSCs (iPSC-MSCs) transduced with a lenti virus vector containing. pCMV-cytosine deaminases/UPRT-P2A- copGFP. Isolated EVs by brightfield and fluorescence. Some of the EVs contain GFP.
Figure 12B:
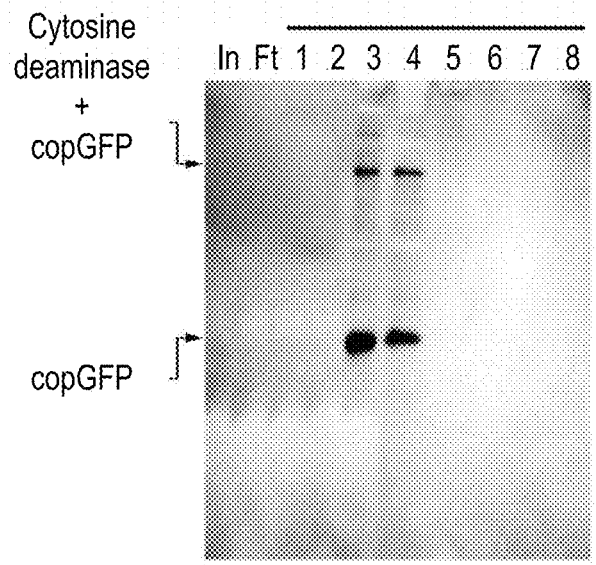
FIG. 12b—Western blot assay demonstrating presence of GFP in the EV preparation. The minor band is a fusion protein with cytosine deaminase/UPRT produced by incomplete cleavage at the P2A cleavage site.
Figure 12C:
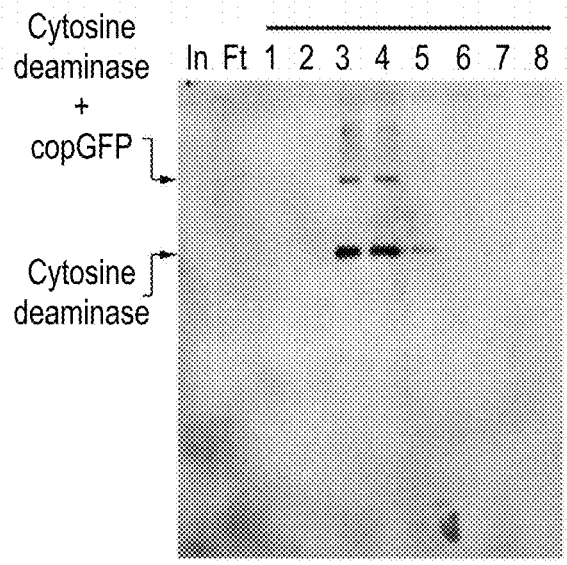
FIG. 12c—Western blot assay demonstrating presence of cytosine deaminase in the EV preparation. The minor band represents incomplete cleavage at the P2A site.

In this study, the efficacy of intranasal administration of extracellular vesicles (EVs) generated from human bone marrow derived mesenchymal stem cells for suppressing SE-induced inflammation, was examined. The results are presented at FIG. 12.

Example 9—Selection of Optimal MSCs and Culture Conditions for Production of EVs Preparations of tissue-derived MSCs vary in their characteristics dependent on undefined properties of the human donor of the tissue and the site from which the cells are obtained from the same donor. Therefore, a preparation of human bone marrow MSCs (defined as donor 6015), was selected from our NIH-sponsored center for distribution of MSCs, that met the classical in vitro criteria for MSCs and that ranked among the top 3 of 13 MSC preparations in expression of the biomarker of mRNA for TSG-6 that was highly correlated with the efficacy of the cells in modulating inflammation in three murine models (34). MSCs also vary with culture conditions, such as cell densities, and the culture medium (6). To reduce the variability, we followed a protocol in which the MSCs were consistently plated at 500 cells per cm2 in a standardized medium (21-24) containing 17% of a pretested batch of FBS [defined as complete culture medium (CCM)].

Figure 13A:
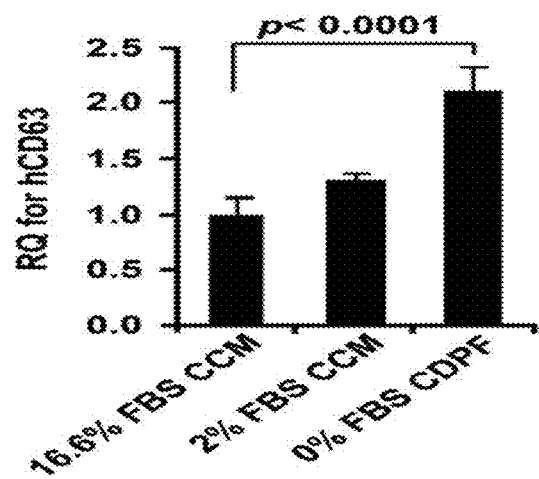
FIG. 13a—Defining conditions for production of EVs. Cultures of human MSCs (donor 6015) at 70-80% confluent were transferred to the media indicated and incubated for 6-48 h.
Figure 13B:
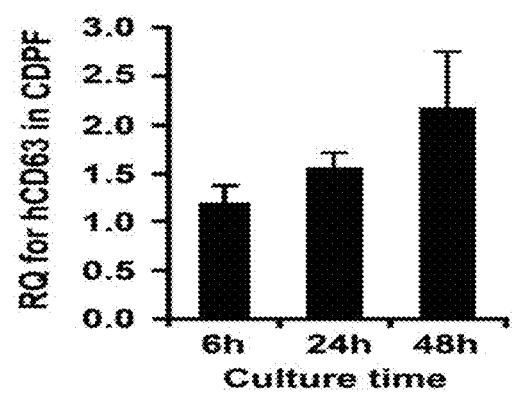
FIG. 13b—Expression of mRNA for CD63 was increased by culture for 48 h in CDPF medium compared with culture in CCM with standard concentration of FBS (16.6%) or reduced FBS (2%). Assay by RT-PCR. Expression of mRNA for CD63 was increased with time of incubation in CDPF.
Figure 13C:
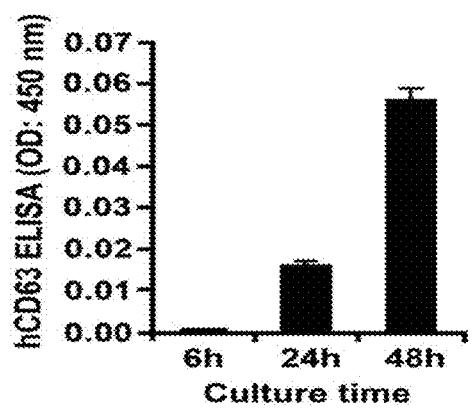
FIG. 13c—Secretion of CD63+ was increased with time in CDPF. Medium was assayed by ELISA for vesicle-bound protein.
Figure 13D:
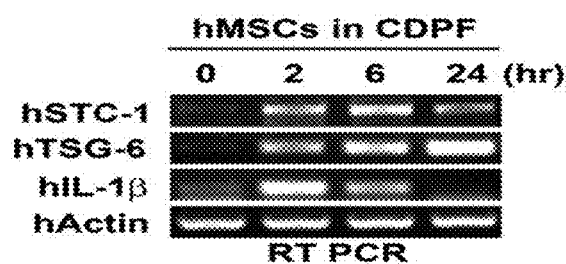
FIG. 13d—RT-PCR assays in MSCs incubated in CDPF indicated that the proinflammatory cytokine IL-1β was expressed for up to 6 h and that expression of the inflammation-modulating protein TSG-6 increased between 2 and 24 h. Expression of the antiapoptotic/calcium-phosphate metabolic protein STC-1 peaked at about 6 h.
Figure 13E:
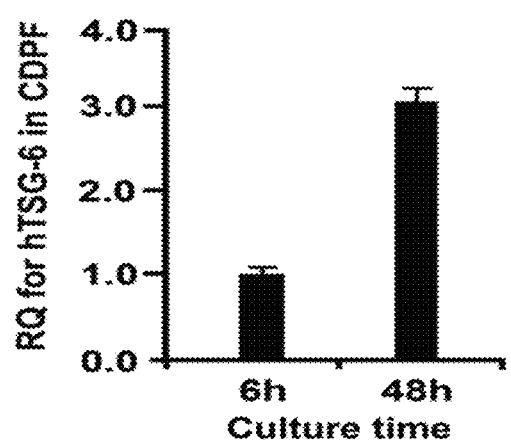
FIG. 13e—Expression of mRNA for TSG-6 increased with time of incubation in CDPF.
Figure 13F:
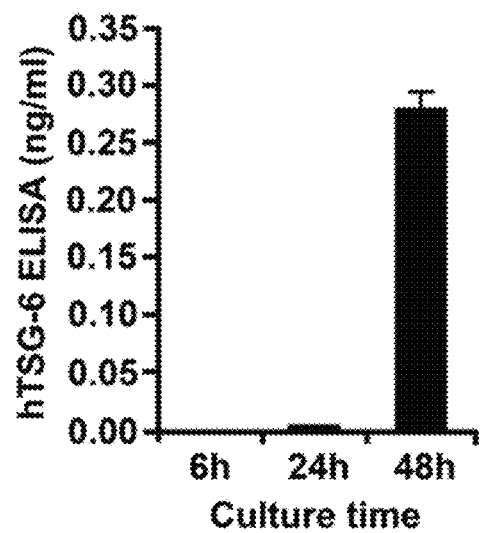
FIG. 13f—Secretion of TSG-6 increased with time in CDPF. Assay by ELISA.
Figure 13G:
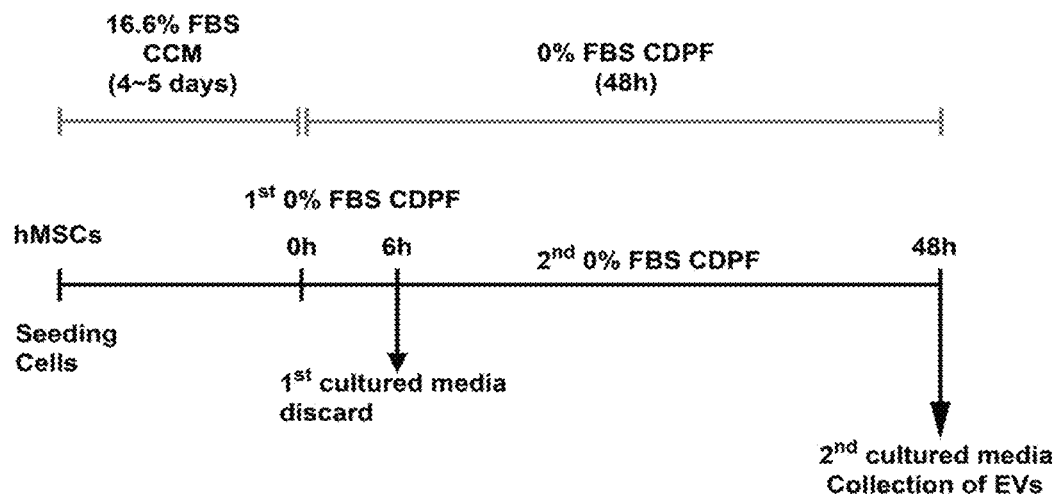
FIG. 13g—Schematic for protocol developed for production of EVs by MSCs.
Figure 14A:
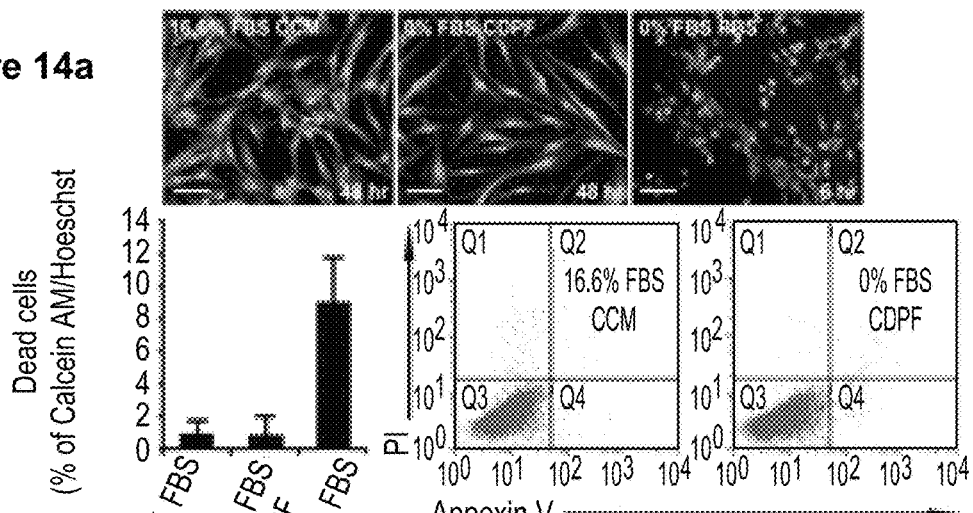
FIG. 14a—Survival of the MSCs under the culture conditions, comparisons of four donors, and demonstration that most of the secreted proteins and EVs are anionic. Survival of MSCs in CDPF. MSCs were expanded to about 70% confluence and then incubated an additional 48 h in CCM, CDPF, or PBS. (Top) Cultures labeled with Hoechst, Calcein AM, and propidium iodide (PI) demonstrate viable cells in CDPF but not PBS. (Bottom) Assays of the same cultures by flow cytometry after labeling with PI and Annexin V demonstrated survival in CCM or CDPF medium but not PBS.
Figure 14B:
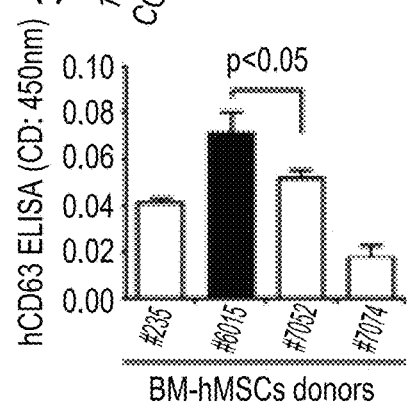
FIG. 14b(i)—Comparisons of four different preparations of MSCs (donors 235, 6015, 7052 and 7074) after incubation (i) CD63+ in medium assayed by ELISA.
Figure 14B:
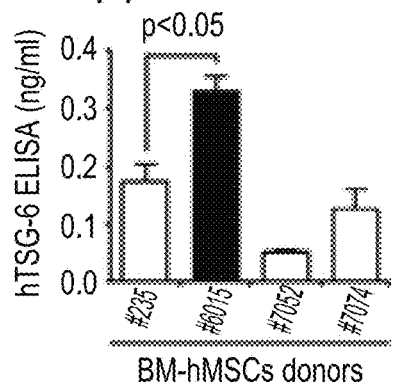

The CCM was replaced after 2 or 3 d. After 5 d, the medium was changed to a proprietary chemically defined and protein medium (CDPF) that was initially optimized by a commercial supplier for production of recombinant proteins by Chinese hamster ovary cells (Invitrogen). We further supplemented the medium (Table 51) to minimize aggregation of cells secreting TSG-6 by cross-linking hyaluronan on the cell surface. As a convenient marker for EVs, we used assays for CD63 (FIG. 51), a tetraspan protein frequently found in EVs (26-29). Culture of MSCs in the CDPF medium increased the expression of mRNA for CD63 (FIG. 13a). The expression of the mRNA increased for at least 48 h and was accompanied by the accumulation of the CD63 protein in the medium (FIG. 13b and FIG. 13c). However, the pattern of genes expressed differed during the time of incubation in the CDPF. At 2 h, there was a high level of expression of mRNA for IL-1β, a major proinflammatory cytokine. In contrast, expression of mRNA for the inflammation-modulating protein TSG-6 was low at 2 h and increased progressively at 6, 24, and 48 h (FIG. 13d and FIG. 13e). The TSG-6 protein in medium did not increase until about 48 h (FIG. 13f). On the basis of these observations, we developed a standardized. protocol for production on EVs that might have anti-inflammatory properties (FIG. 13. The MSCs did not expand, but there was little evidence of cell death (FIG. 14a). Comparison of preparations of MSCs demonstrated that the levels of CD63 protein in the harvested medium were higher in MSCs from donor 6015, the preparation initially selected here, than in three other preparations (FIG. 2b(i)). As expected, the level of TSG-6 in the harvested medium was the highest in donor 6015 (compare FIG. 2b(ii), with FIG. 4a).

Figure 14C:
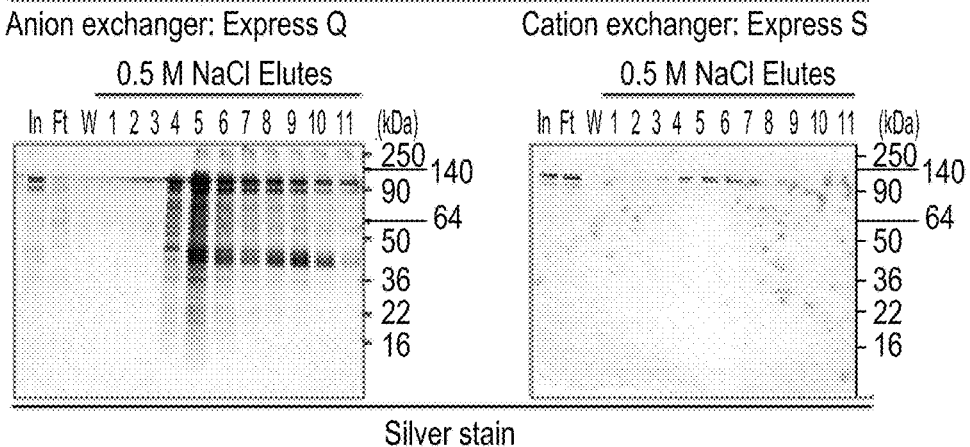
FIG. 14c—(Left panel) Small-scale assays in SDS-electrophoretic gels demonstrated that most of the medium proteins bound to and were eluted from an anionic resin.
Figure 15A:
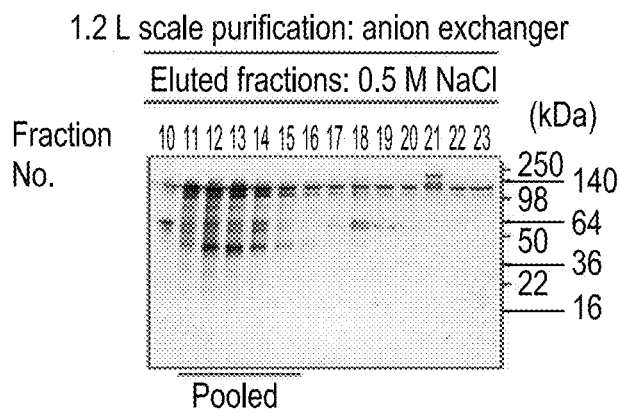
FIG. 15a(i)—Chromatographic isolation and characterization of EVs from the medium. Preparation and characterization of CD63+ EVs from medium of MSCs incubated as described. Assay by SDS-electrophoretic gel of medium eluted from anion exchange column with 0.5 M NaCl. Gel was silver-stained.
Figure 15A:
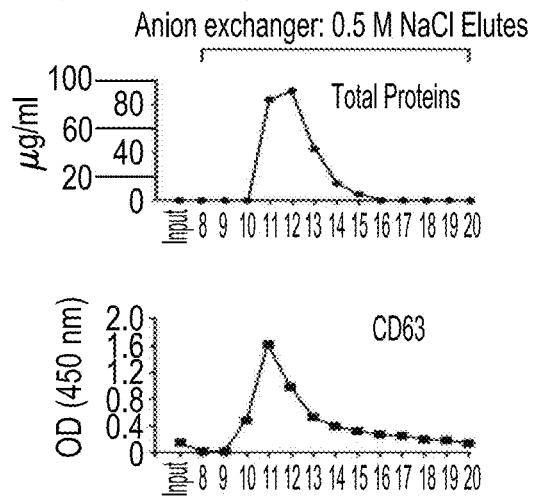
Figure 15B:
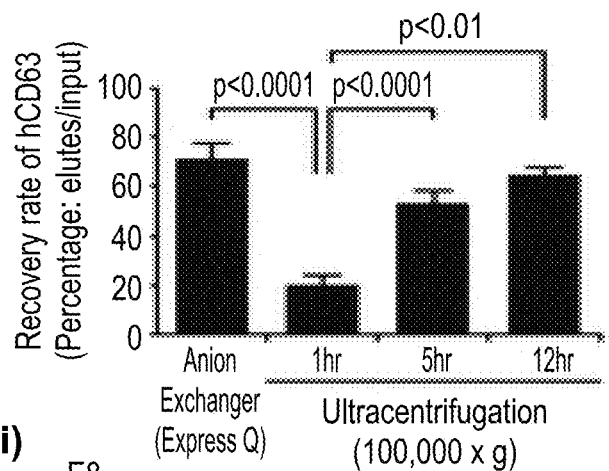
FIG. 15b—Recovery of CD63+ protein from the column was slightly greater than recovery by centrifuging the same samples at 100,000×g for 12 h.

Example 10—Isolation of EVs from Human Tissue Culture Media with a Scalable Protocol Most of the published protocols for isolation of EVs involve high-speed centrifugation or other procedures that cannot be readily scaled up for largescale production (29). To develop a scalable protocol, EVs were harvested from culture medium from a human cell culture by chromatography. In a small scale test, it was determined that most of the protein in the harvested medium bound to an anion exchange resin but that little bound to a cation exchange resin (FIG. 14c). Therefore, a protocol was developed in which the harvested medium was centrifuged at 2,500×g for 15 min and the supernatant was chromatographed on an anion exchange column. The protein eluted with 0.5 M NaCl was recovered as a single broad peak that contained CD63 (FIG. 3a(i) and FIG. 3a(ii)). The recovery of CD63 in the peak ranged from 73% to 81% (n=3) and was slightly higher than was obtained by centrifuging the harvested medium at 100,000×g for 12 h (FIG. 15b).

Figure 15C:
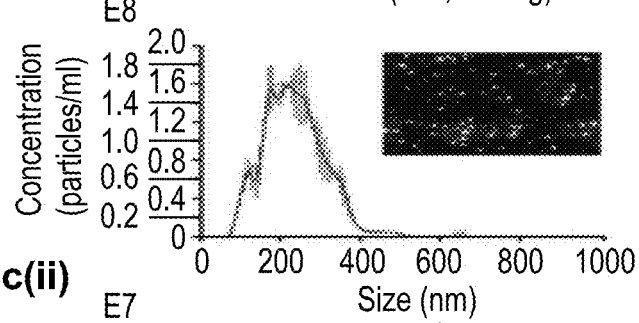
FIG. 15c(i)—Assays of eluted fractions by nanoparticle diffusion analysis demonstrated that the mean size of the vesicles ranged from 209±1.8 nm (SEM) to 231+3.2 nm.
Figure 15C:
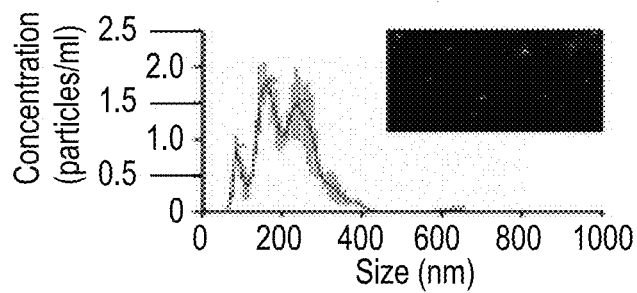

Assay of the peak fractions with a nanoparticle tracking system (FIG. 15c) demonstrated that they contained about $0.51 \times 10^9$ vesicles per microgram of protein. Assays at decreasing concentrations indicated that the mean size of the vesicles was 231±3.2 nm (SEM), 216±2.3 nm, and 207±1.8 nm, respectively. A range of size for the n-EVs would therefore be described as between about 200 nm to about 250 nm for this particular assay at the decreasing concentrations. The three peaks observed at the lowest concentration were 85, 165, and 236 nm, the expected sizes of EVs of 85 nm that were also recovered as dimers and trimers.

Example 11—Surface Epitopes of the Isolated EVs

To map surface epitopes, the method of Oksvold (2015) was used. In this method, the EVs were first trapped with a large bead linked to an antibody to CD63, and then additional epitopes on the trapped EVs are assayed with standard protocols for flow cytometry. The initial population of EVs captured with the protocol were positive for CD63. They were also about 80% positive for CD81, another epitope frequently found on EVs. However, the EVs of the present preparations selected according to the techniques and under the conditions described herein, isolated from cells of human origin, were determined to be negative for CD9. CD9 is an epitope that has been described as being present on EV preparations of others. The n-EVs of the present studies (also being referred to herein as hn-EV's (human n-EVs) were also characterized as being negative for 13 additional epitopes. (See Table 2). These 13 additional epitopes are typically found on the surface of hMSCs.

TABLE 2

Surface epitopes in hMSCs and hEVs.

| Surface epitopes | hMSCs* CCM | CDPF | hEVs* |
| --- | --- | --- | --- |
| hMSC markers | | | |
| CD29 | >99 | >99 | <1 |
| CD44 | >99 | >99 | <2 |
| CD49c | >99 | >99 | <1 |
| CD49f | >99 | >99 | <1 |
| CD59 | >99 | >99 | 2.04 |
| CD73 | >99 | >99 | <2 |
| CD90 | >99 | >99 | <1 |
| CD105 | >99 | >99 | <1 |
| CD146 | >99 | >99 | <2 |
| CD147 | >99 | >99 | <1 |
| CD166 | >99 | >99 | <1 |
| HLA-a, b, c | >99 | >99 | <2 |
| PODXL | 95 | 91 | <2 |
| EV markers | | | |
| CD9 | 93 | 99 | <1 |
| CD63 | 48 | 85 | 90.6 |
| CD81 | >99 | >99 | 79.9 | hMSC, human mesenchymal stem/stromal cell.
*Positively stained cells or EVs (% of total) with specific antibodies indicated.

Example 12—In Vivo Assay for Efficacy of n-EV Preparations in Suppressing Neuroinflammation after Traumatic Brain Injury (TBI)

Figure 16A:
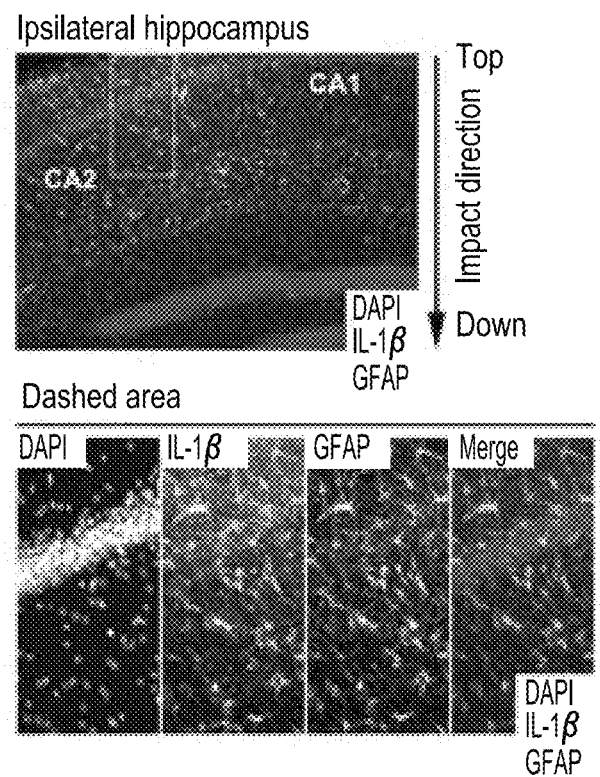
FIG. 16a—Dose-response data for suppression of neuroinflammation by EVs after TBI Immunochemistry of brain sections demonstrated that TBI increased IL-1β in GFAP+ astrocytes. Sections from brain recovered 12 h after TBI and sections from region indicated were stained for DAPI, IL-1β, and GFAP. 16B—Dose-dependent decrease in IL-1β after i.v. administration of PBS or EVs. Amounts varied from 3.5 to 30 µg of protein or $1.8-15.3 \times 10^9$ EVs. PBS or EVs were administered 1 h after TBI, and assays were by ELISA on homogenates of ipsilateral brain isolated 12 h after TBI. The i.v. administration of 1 million MSCs cultured in CCM had little effect, apparently because they were not fully activated in 12 h to express TSG-6 by embolization of the lung.
Figure 16B:
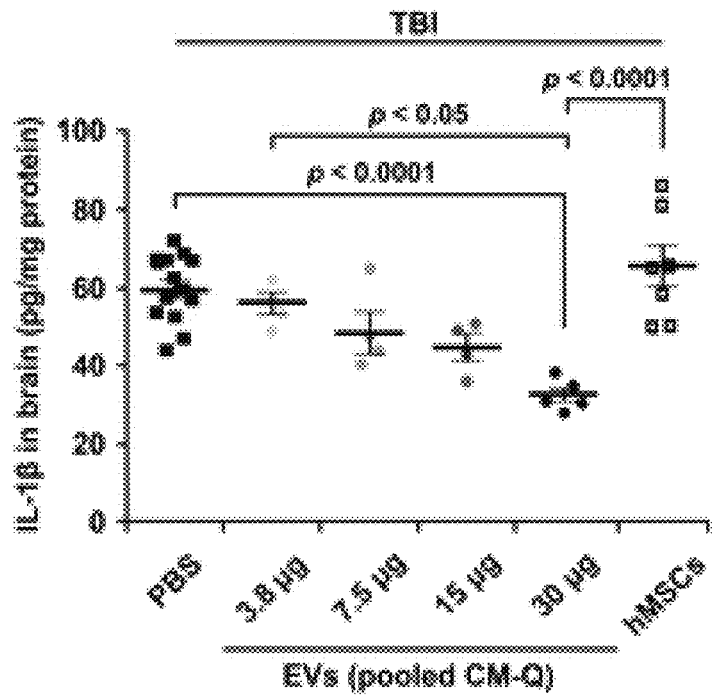

A quantitative assay for the efficacy of EVs was developed as a model for TBI using an ELISA performed on brain homogenates. The present inventors initial studies demonstrated that, after TBI, levels for the proinflammatory cytokine IL-1β peaked between 6 and 12 h and that the IL-1β colocalized with GFAP+ astrocytes (FIG. 16a). Therefore, a protocol was followed in which TBI was produced in mice, and then IL-1β levels in the brain homogenates made from tissue of these TBI mice was assayed 12 h after the TBI. Administration of the EVs decreased the levels of IL-1β in a dose-dependent manner (FIG. 16b). The highest dose of EVs was more effective than i.v. infusion of 1 million of MSCs expanded in CCM. This may be because the brains were assayed 12 h after administration of the cells, while i.v.-administered MSCs that are trapped in the lung do not express high levels of TSG-6 until 24 h after infusion. The dose of EVs that produced the largest effect (30 µg of protein and $15 \times 10^9$ EVs) was synthesized by about 1 million MSCs under the conditions used here (FIG. 16g), but the in vitro and in vivo data are directly comparable. Of special interest was a result in which the dose of EVs that produced the largest effect (30 µg of protein and $15 \times 10^9$ EVs) contained only 4 ng of TSG-6 whereas administration of 50 µg of recombinant TSG-6 i.v. was required previously in four models of induced inflammation in mice (21-23).

After i.v. administration of 30 µg of CD63+ EVs into naive mice, the EVs were detected by ELISAs of plasma after 5 min, but they were not detected after 15 min. Therefore, the EVs were apparently rapidly distributed to tissues. Low levels of CD63+ EVs were also detected in plasma 5 min after infusion of $1 \times 10^6$ MSCs from donor 6015.

Figure 17A:
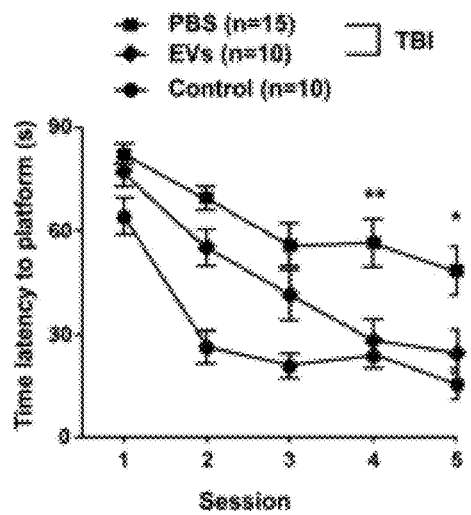
FIG. 17a—Improved cognitive function after TBI and i.v. EVs. About 1 h after TBI, each mouse received i.v. PBS or 30 µg of protein (about $15.3 \times 10^9$ EVs) from the pooled peak from the anion exchange column (pooled CM-Q). Behavior in the water maze was tested 28-33 d after TBI. The pattern separation test was performed 35 d after TBI.
Figure 17B:
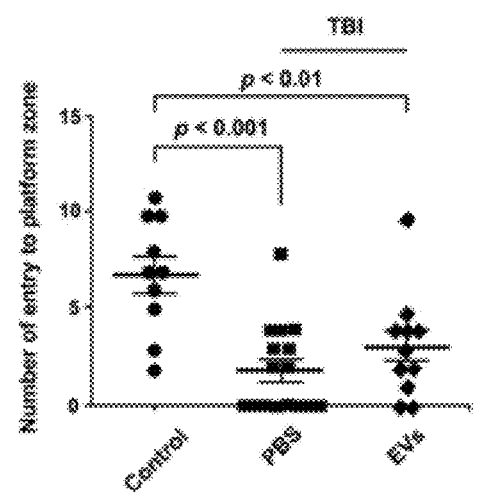
FIG. 17b—In the water maze, treated mice with TBI learned to locate the hidden platform with the same latency as controls after four trials and better than TBI mice that received PBS.
Figure 17C:
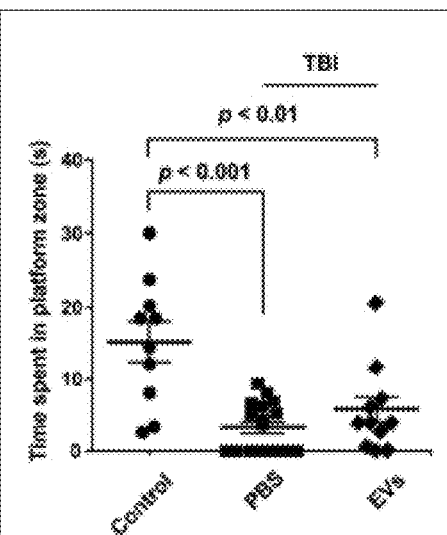
FIG. 17c—There was no significant effect of the therapy on the number of entries to platform zone, or FIG. 17d—Time spent in the platform zone in the probe test. The treated mice performed better than TBI mice that received PBS in the pattern separation test.
Figure 17D:
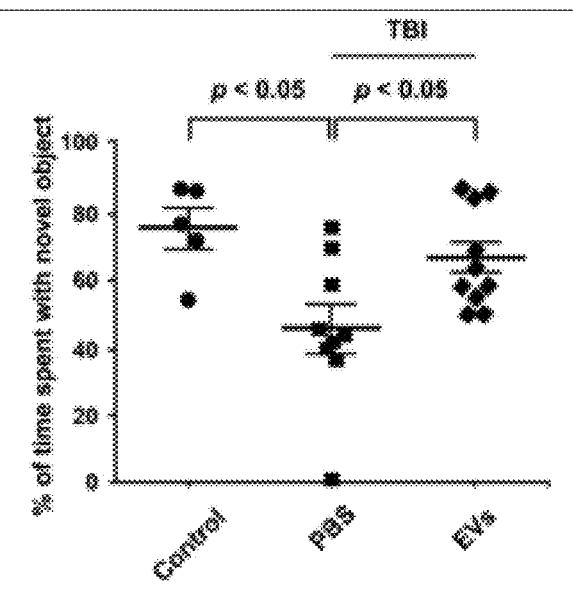
Figure 18A:
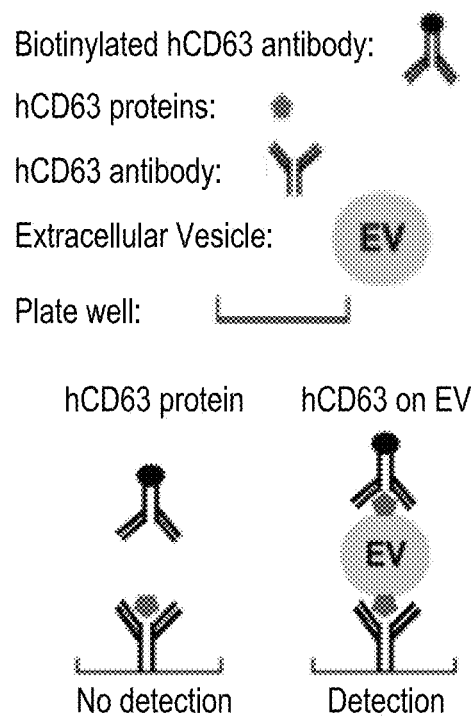
FIG. 18a—ELISA for $CD63^+$ proteins on EVs. Schematic of the assay.
Figure 18B:
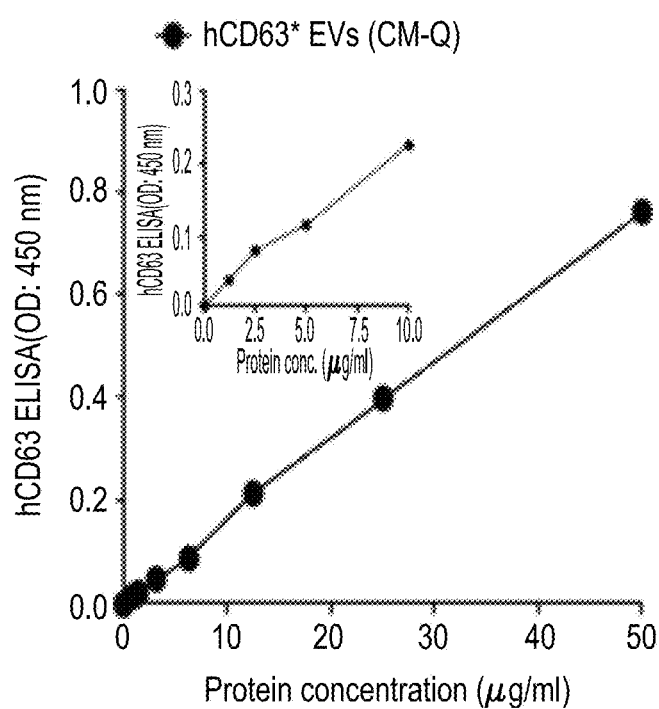
FIG. 18b—Standard curve prepared with varying amounts of protein from pooled fractions of column. Assays by nanoparticle diffusion analysis indicated 1 µg=$0.51 \times 10^9$ EVs.
Figure 19:
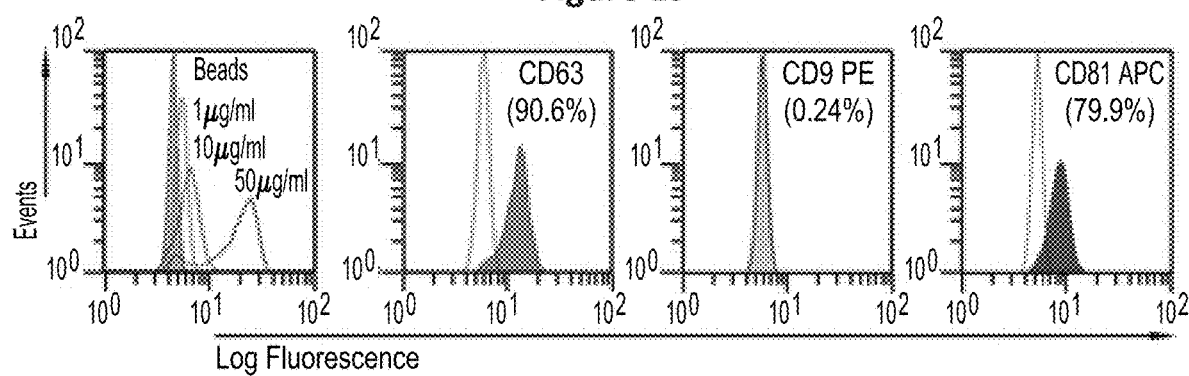
FIG. 19—Assays of epitopes on the isolated EVs. The EVs were trapped on a magnetic bead covalently linked to anti-CD63 and then assayed for additional epitopes by flow cytometry. Data were gated for single beads. (Left) Detection of CD63 as a function of the concentration of protein added. In the remaining panels (right), EVs were positive for CD63 and CD81 but not for CD9.
Figure 20:
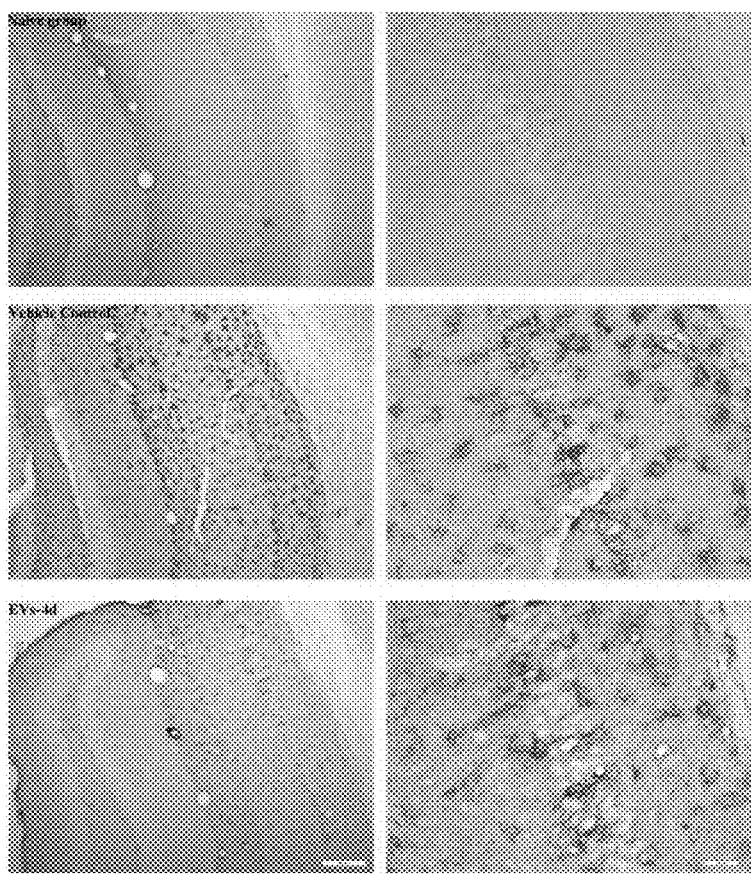
FIG. 20—ED-1 staining in the hippocampus of a naive control mouse (top panels), a mouse receiving vehicle after SE (middle panels), and a mouse receiving EVs after SE (lower panels). Note an increased density of activated microglia in the dentate gyrus and CA1 subfield of a mouse receiving vehicle after SE (middle panels). However, the density of activated microglia in these regions is clearly decreased in a mouse receiving EVs after SE (lower panels). Left hand panel are 10× and right hand are 20× of regions of same sections.
Figure 21:
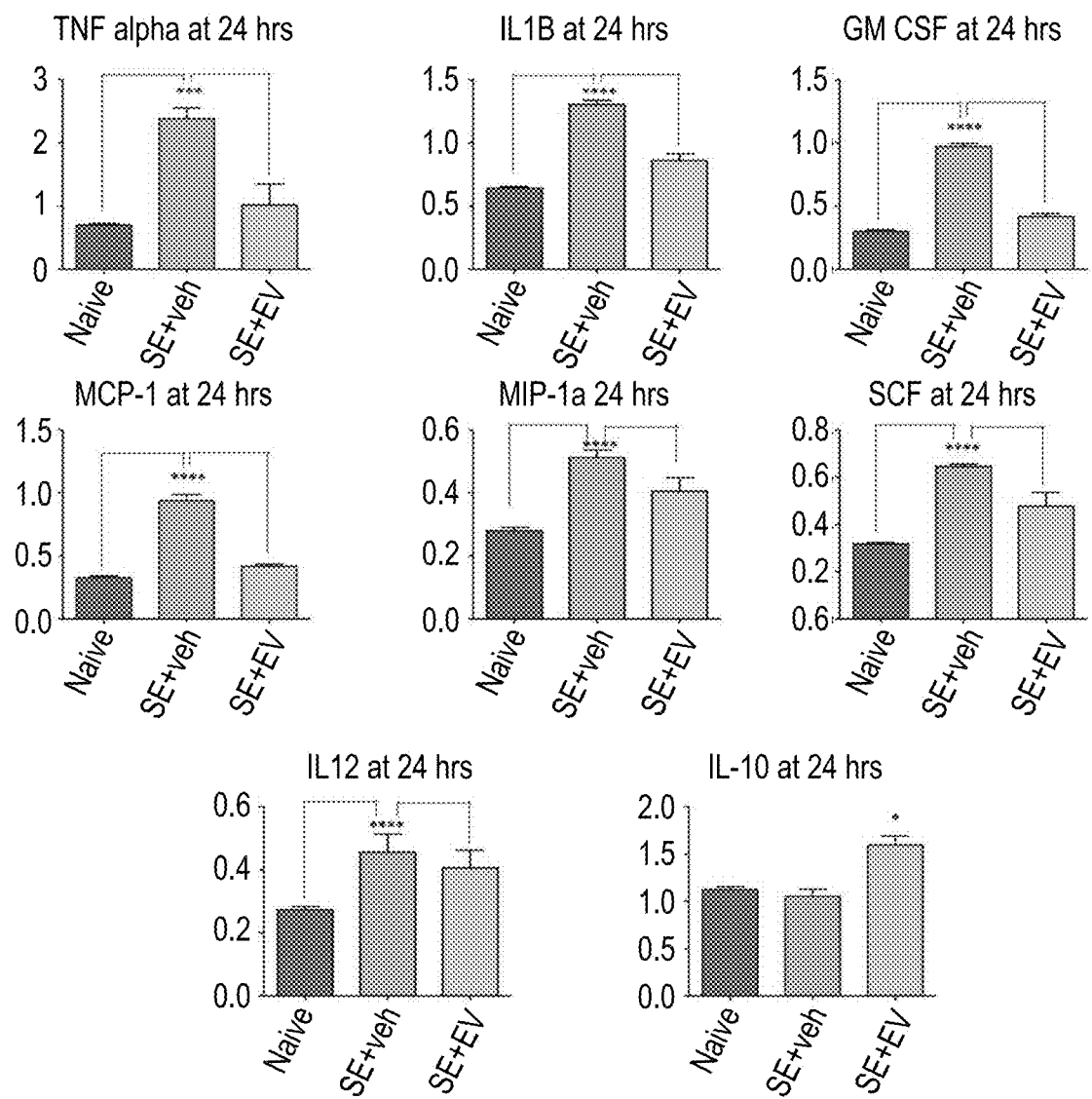
FIG. 21—ELISAs for cytokines in hippocampus. Seizures were induced in mice with pilocarpine as in FIG. 2. Two hours after onset of status epilepticus (SE), the mice received 7.5 billion exosomes (EV) intranasally. The animals were killed 24 hours later, the hippocampi isolated, and the tissues assayed for 24 cytokines with an ELISA kit (Mouse Cytokine ELISA Plate Array Colorimetric; cat. #EA-40005; Sognosis). The 7 cytokines that were increased with SE+ vehicle (veh) are pro-inflammatory. Their decrease with intranasal exosomes (SE+EV) indicates that the exosomes decreased the induced inflammation in the hippocampus. IL-10 is a cytokine secreted by regulatory T cells and other cells than suppress immune reactions. The increase in IL-10 with intranasal exosomes indicates the exosomes decrease immune responses to the injury to brain. *$p<0.05$; * $p<0.001$; **$p<0.0001$.

Example 13—In Vivo i.v. Infusion of Isolated n-EV Preparations after TBI Rescues Pattern Separation and Spatial Learning Impairments Because the isolated EVs decreased inflammation 12 h after TBI, the effects of these n-EVs of human cell origin were examined for effect on pattern separation ability and spatial learning and memory function a month after TBI (FIG. 17). The present example demonstrates that the present preparations provide for rescue of pattern separation impairment and spatial learning impairment attendant TBI, and also establishes the utility of the present preparations and methods for treating milder forms of TBI, such as concussion. Pattern separation is proficiency for discriminating analogous experiences through storage of similar representations in a nonoverlapping manner (37, 38), and the hippocampus neurogenesis plays a major role in maintaining this function. An object-based behavioral test demonstrated preservation of the ability for pattern separation in TBI mice treated with i.v. EVs, in comparison with TBI mice treated with vehicle exhibiting pattern separation deficits (FIG. 17d). Furthermore, in a water maze test (FIG. 17a), TBI mice treated with i.v. EVs learned to find the concealed platform after three trials as reflected in the decrease in latency time that became similar to the latency time in control mice that received sham operations, implying preservation of spatial learning ability in TBI mice receiving EVs. In contrast, mice that received vehicle after TBI improved only slightly. There were no significant differences in memory retrieval function in a probe test between TBI mice receiving EVs or vehicle because the number of times mice entered the platform zone and the time spent in the platform zone (FIG. 17b and FIG. 17c) were similar between the two TBI groups, which contrasted with the behavior of control mice exhibiting greater dwell times in the platform zone.

Example 14—Supplementary Materials and Methods Culture Conditions for Producing EVs The details for the various methods, including culture conditions, chromatographic isolation of EVs, PCR and ELISA assays, a nanoparticle tracking analysis tracking, controlled cortical impact injury, behavioral studies, and statistical tests, are presented. hMSCs were obtained from normal, healthy donors with informed consent.

Culture Conditions for Producing EVs. A frozen vial of passage 4 MSCs was thawed at 37° C. and plated directly at about 500 cells per cm2 in 150×20-mm-diameter tissue culture plates (cat. no. 430599; Corning) in complete culture medium (CCM). The CCM medium was replaced after 2-3 d. After the cells reached about 70% confluency in 4-6 d, the medium was replaced with a medium optimized for Chinese hamster ovary cells (CD-CHO Medium; cat. no. 10743-002; Invitrogen) that was further supplemented to prevent aggregation of cells synthesizing TSG-6 (Table 1).

100×MEM vitamin solution 10 mL 11120-052; Invitrogen.
*A mixture of hypoxanthine (10 mM) and thymidine (1.6 mM).
The medium was recovered after 6 h for assays and discarded. The medium replaced and the medium recovered between 6 and 48 h was either stored at −80° C. or used directly to isolate EVs.

Isolation of EVs by Chromatography. Experiments were carried out with medium harvested from four or five 15-cm-diameter plates and tested for binding of the protein to a cation exchange resin (Express S; cat. no. 40792025; Whatman) or an anion exchange resin (Express Q; cat. no. 4079302; Whatman). For isolation of EVs, medium harvested from 40 to 45 plates (about 1.2 L) was used directly or after thawing. The medium was centrifuged at 2,565×g for 15 min to remove cellular debris, and the supernatant was applied directly at room temperature to a column containing the anion exchange resin (100-mL bed volume) that had been equilibrated with 50 mM NaCl in 50 mM Tris buffer (pH 8.0). The medium was applied at a flow rate of 4 mL/min and at room temperature. The column resin was washed with 10 volumes of the equilibration buffer and then eluted with 25 volumes of 500 mM NaCl in 50 mM Tris buffer (pH 8.0). Fractions of 20-30 mL were collected and stored at either 4° C. or −20° C.

Human MSCs from Bone Marrow. Passage 1 WT MSCs (anonymously identified as from donors 235, 6015, 7052, and 7074) were isolated from bone marrow aspirates and cultured as previously described (38) For the experiments described here, a frozen vial of about 1 million passage 1 MSCs was thawed at 37° C. and plated in CCM consisting of a-minimum essential medium (α-MEM; Gibco), 17% (vol/vol) FBS (Atlanta Biologicals), 100 units/mL penicillin (Gibco), 100 μg/mL streptomycin (Gibco), and 2 mM L-glutamine (Gibco) on a 152-cm$^2$ culture dish (Corning). After 15-24 h, the medium was removed, the cell layer was washed with PBS, and the adherent viable cells were harvested using 0.25% trypsin and 1 mM EDTA (Gibco) for 3-4 min at 37° C., reseeded at 500 cells per cm$^2$ in CCM, and incubated for 5-7 d (with medium change on day 3) until 70-80% confluency (from 6,000-10,000 cells per cm$^2$). The medium was removed, the cell layer was washed with PBS, and the cells were lifted with trypsin/EDTA and frozen at a concentration of about 1 million cells per mL in α-MEM containing 30% (vol/vol) FBS and 5% (vol/vol) dimethyl sulfoxide (Sigma). For the experiments here, the cells were expanded under the same conditions, and passage 4 cells were used.

RT-PCR and Real Time PCR Assays. RNA extraction and cDNA synthesis were performed as described. (Lee et al (2014), PNAS, 111 (47): 16766-16771). The synthesized cDNA was amplified by Ex Taq DNA Polymerase (TaKaRa) and the following primers:

```
human STC-1,
sense
ATGCTCCAAAACTCAGCAGTG, antisense
TATGCACTCTCATGGGATGTGC;

human TSG-6,
sense
TCACATTTCAGCCACTGCTC, antisense
AGACCGTGCTTCTCTGTGGT;

human IL-1β,
sense
GCACGATGCACCTGTACGAT, antisense
CACCAAGCTTTTTTGCTGTGAGT, human β-actin,
sense
AGGCACCAGGGCGTGAT, antisense
GCCCACATAGGAATCCTTCTGAC.
```

Realtime amplification was performed using a TaqMan Universal PCR Master Mix and primers [human CD63, Hs01041237; human TSG-6, Hs01113602; human GAPDH, Hs0275891 (Life Technologies)] and was conducted with the 7900HT fast real-time PCR system (Life Technologies). The mRNA levels were normalized to the level of GAPDH.

Live and Dead Cell Staining. hMSCs (1×105) were incubated in CCM on a six-well plate. After 24 h, medium was changed to a different concentrated FBS. After incubation of hMSCs with 16.6% (vol/vol) FBS, 0% FBS CDPF for 48 h, or 0% FBS PBS for 4 h, cells were stained with Hoechst (Thermo) and a LIVE/DEAD Cell Imaging Kit (Molecular Probes) for 15 min at 25° C., and then live fluorescence was visualized using a microscope (Nikon Eclipse 80i). The possibility that the CDPF induced apoptotic cell death of hMSCs was assessed by using the Annexin V-FITC apoptosis detection kit (Sigma) according to the manufacturer's instructions. After culture with the CDPF, 1×106 cells per 300 μL were resuspended in Annexin V binding buffer and stained with Annexin V-FITC and PI for 10 min at room temperature. The cells were analyzed by a FC500 flow cytometer [Beckman-Coulter].

Isolation of EVs by Ultracentrifugation. To compare the yield of EVs containing CD63, EVs were isolated by ultracentrifugation. The medium was centrifuged 2,565×g for 15 min to remove cells and debris and centrifuged at 100,000×g (Sorvall WX Floor Ultra Centrifuge and AH-629 36 mL swinging Bucket Rotor; Theinio) for 1, 5, and 12 h at 4° C. EVs were stored in PBS at 4° C. or −20° C. EV protein content was quantified by the Bradford method (Bio-Rad).

ELISA for CD63+ EVs. A 96-well plate (cat. no. 441653; Nunc) was coated with monoclonal 5 μg/mL anti-CD63 antibody (clone H5C6, cat. no. 556019; Becton-Dickinson) in a volume of 50 μL per well of carbonate buffer (pH 9.4)

and incubated overnight at 4° C. After three washes with PBS containing 0.1% Tween 20, 100 µL per well of blocking solution (PBS containing 1.0% BSA) were added at room temperature for 1 h. After one wash in PBS containing 0.1% Tween 20, intact extracellular vesicles were captured in a 96-well at a final volume of 100 µL and incubated for 3 h at room temperature. After three washes with PBS containing 0.1% Tween 20, biotinylated anti-CD63 antibodies (clone H5C6, cat. no. 353018; BioLegend) diluted to 4 µg/mL were added and incubated for 1.5 h at room temperature. After three washes with PBS containing 0.1% Tween 20, the plate was incubated with 50 µL of streptavidin-horseradish peroxidase (R&D Systems) diluted 1:200 in PBS for 20 min at room temperature. After the final four washes with PBS containing 0.1% Tween 20, the detection substrate reagent (cat. no. DY999; R&D Systems) was added at 100 µL per well and incubated for 4 min. The response was blocked with 0.1 mL of 1 M H2SO4, and optical densities were recorded at 450 nm. The standard curve prepared with pooled peak from FIG. 3a(ii), was linear over a range of about 1-50 µg of protein.

Surface Markers of EVs. The assay was performed as described by Oksvold et al. (2015) Meth. Mol. Biol. 1218: 465-481). Human anti-CD63-coated magnetic beads (40 µL, cat. no. 106-06D; Life Technologies) were washed with PBS and mixed with 100 µL of samples. The mixture was incubated at 4° C. overnight with rotation, after which unbound or excess extracellular vesicles were removed using a magnetic rack (DynaMag-Spin; Life Technologies) to capture the beads and wash the beads twice with 500 µL of PBS containing 0.1% BSA. The washed beads were released from the rack and resuspended in 300 µL of PBS containing 0.1% BSA. The samples were incubated with the conjugated antibodies at room temperature for 30 min with rotating in the dark. The stained samples were washed twice by using a magnetic rack with PBS containing 0.1% BSA. The samples were assayed on a FC500 flow cytometer (Beckman-Coulter; with antibodies indicated in Table 3, Antibodies used for flow cytometry analyses.

TABLE 3

Antibodies used for flow cytometry analyses

| Antibody | Origin | Vendor | Catalog no. |
|---|---|---|---|
| hMSC markers | | | |
| CD29 | mIgG-1 | GD Biosciences | 559882 |
| CD44 | mIgG-2b | GD Biosciences | 559942 |
| CD49c | mIgG-1 | GD Biosciences | 556025 |
| CD49f | rIgG-2a | GD Biosciences | 551129 |
| CD59 | mIgG-2a | Beckman | IM3457U |
| CD73 | mIgG-1 | GD Biosciences | 550257 |
| CD90 | mIgG-1 | Beckman | IM3703 |
| CD105 | mIgG-3 | Beckman | A07414 |
| CD146 | mIgG-2a | Beckman | A07483 |
| CD147 | mIgG-2 | GD Biosciences | 555962 |
| CD166 | mIgG-1 | Beckman | A22361 |
| HLA-a, b, c | mIgG-1 | GD Biosciences | 555552 |
| PODXL | mIgG-2a | MGL | M084-4 |
| EV Markers | | | |
| CD9 | migG-1 | GD Biosciences | 341647 |
| CD63 | migG-1 | GD Biosciences | 557288 |
| CD81 | migG-1 | GD Biosciences | 551112 |

Assay of EVs with Nanoparticle Tracking Analysis. The concentration and size distribution of particles were measured by nanoparticle tracking analysis (Nanosight LM10; Malvern). Temperature was monitored throughout the measurements. For all our recordings, we used a camera level of 13 or 14 and automatic functions for all post-acquisition settings, except for the detection threshold, which was set at 5. The instrument was standardized with polystyrene latex microsphere [cat. no. NTA4088 (100 nm) and no. NTA4089 (200 nm)] beads. Samples were diluted to achieve a particle count of between $2\times10^8$ and $1\times10^9$ per milliliter. They were dispersed briefly before the assay to dissociate aggregates.

Controlled Cortical Impact Injury. All animals were treated in accordance with a protocol approved by the Institutional Animal Care and Use Committee of Texas A&M Health Science Center College of Medicine. Male C57BL/6J mice were purchased from The Jackson Laboratory and were 7-8 wk old at the time of controlled cortical impact (CCI). A CCI device (eCCI Model 6.3; Custom Design and Fabrication at Virginia Commonwealth University Medical Center) was used to induce TBI. Mice were anesthetized with 3% (vol/vol) sevoflurane in O2 and mounted in a stereotactic frame. An ~4-mm craniotomy was performed over the right parietal cortex between the bregma and the lambda sutures. The impact, with a velocity of 4.5 m/s and a dwell time of 250 ms and a deformation depth of 1.0 mm using a 3-mm-diameter impactor tip was applied. After the injury, the bone fragment was put back in place and a disk made from dental cement was adhered to the skull using Vetbond tissue adhesive (3M). The scalp was fastened with sutures. Body temperature was maintained at 37° C. using a heating pad. One hour after CCI, the mouse was placed in a tail vein injection restrainer with warming water bath (40° C.), which restrained the animal and gently warmed the tail while allowing access to the tail vein. The hMSCs (donor 6015, 1×106 cells per mouse) or chromatographically concentrated CCM (3.8, 7.5, 15, 30 µg per mouse) in 200 µL of PBS were injected using a 29G insulin syringe.

Immunohistochemistry. Animals: Animals were perfused with 4% (vol/vol) paraformaldehyde in PBS, and the brains were postfixed in the same fixative for 24 h. Brains were then cryoprotected in 20% (vol/vol) sucrose and sectioned (40-50 µm), and subsequent immunostaining was performed by the free-floating method. Briefly, after an antigen retrieval process for 30 min in 10 mM sodium citrate buffer (pH 8.5) at 80° C., the brain slices were blocked and permeabilized with PBS-T (0.2% Triton X-100 in PBS) containing 2% (vol/vol) horse serum for 1 h, incubated with IL-1β (ab9722; Abcam) and GFAP (SC6170; Santa Cruz) antibodies overnight, incubated with Alexa 594-conjugated anti-rabbit IgG, Alexa 488-conjugated antirabbit IgG, and DAPI (1 µg/mL) for 30 min, mounted onto slides, and observed under a microscope (Nikon Eclipse 80i).

ELISA for IL-1β and IL-6 in Brain and for IL-10 in Plasma. Twelve hours after CCI, the mouse was anesthetized with ketamine/xylazine. Blood was recovered by heart puncture in heparin-coated capillary blood collection tubes (Terumo), and it was centrifuged at 3,000×g for 10 min at 4° C. for measuring IL-10 in plasma. The centrifugation step was repeated twice to minimize platelet contamination, and the clear plasma fraction was stored at −80° C. The levels of IL-10 were measured by ELISA kit (R&D Systems). After collection of blood, the mouse was transcardially perfused with PBS. The right side of the injured brain was immediately collected and frozen at −80° C. For protein extraction, the brain was sonicated on ice in lysis buffer PBS containing 1% Triton X-100, protease inhibitor mixture (complete ULTRA Tablet; Roche), and centrifuged at 20,000×g for 10 min at 4° C. Total protein concentrations were measured using a BCA Protein Assay Kit (Thermo) and adjusted to 10 mg/mL. The levels of IL-1β and IL-6 were determined in 0.5 mg of total protein using an ELISA kit (R&D Systems).

Detection of EVs in Plasma. About 30 μg of chromatographically concentrated CM or 1×10$^6$ hMSCs (donors 6015 or 7074) were injected into the tail vein of a C57BL/6J mouse. Blood was collected by cardiac puncture at 0 min, 5 min, 15 min, and 30 min after i.v. injection. The mice were anesthetized with ketamine/xylazine, and blood was recovered in heparin-coated capillary blood collection tubes (Terumo). To separate plasma, the sample was centrifuged at 3,000×g for 10 min at 4° C. The levels of intact extracellular vesicles containing CD63 in plasma were determined by ELISA described above.

Morris Water Maze Test. Mice were tested for spatial learning and memory function in the daylight period on days 28-33 after CCI using the Morris water maze paradigm. The water maze tank, a circular plastic pool measuring 120 cm in diameter and 60 cm in height, was filled with water maintained at 25° C. and made opaque with white paint. The extra-maze visual cues were hung on the walls surrounding the pool, and a hidden platform was submerged 1 cm below the surface of the water. The mouse was first taught to locate a square platform submerged in water within one of the four quadrants, using spatial cues. The swim path of mice in the water maze tank was continuously video-tracked and recorded using the computerized ANY-maze video-tracking system. There were five learning sessions over 5 d with four acquisition trials (90 seconds per one trial) per session, with an inter-trial interval of 120 seconds. For each trial, the mouse was released into the water facing the wall of the pool in a pseudorandom manner so that each trial commenced from a different start location. Once the mouse reached the platform, it was allowed to stay there for 10 s. When the mouse failed to find the platform within the ceiling period of 90 seconds, it was guided into the platform where it stayed for 10 seconds. The location of the platform remained constant across all learning sessions. After each trial, the mouse was wiped thoroughly with dry towels, air-dried, and placed in the home cage. Tracking software (ANY-maze; San Diego Instruments) was used to record latency to find the platform, swim speed, and swim path. From the data, mean values were calculated for each parameter for every learning session and compared between groups. The latency to reach the submerged platform was measured as an indicator of learning ability. On the sixth day of testing (day 33 after CCI), a 90 second retention (probe) test was conducted in which the platform was removed. The mouse was released from a quadrant that was opposite to the position of the platform during learning sessions. The number of entries into the platform area and time spent in the platform area were calculated from the ANY-maze program.

Pattern Separation Test. Pattern separation function is the ability to distinguish between similar experiences that require maintenance of hippocampal neurogenesis (37, 38). Mice are naturally attracted by novel objects, and this behavior can be easily quantified and used to study simple recognition memory in rodents. Mice were tested for pattern separation function in the daylight period on day 35 after CCI. Before starting the test, the mouse was acclimatized to the open field apparatus (45×45 cm each). The test involved three trials. In each trial, the behavior of the mouse was examined for 5 minutes. The apparatus was cleaned with 70% (vol/vol) alcohol and air-dried before the commencement of each trial for every mouse. In the first trial, the mouse was placed with two identical objects (object type 1) in an open field apparatus with a floor pattern (pattern type 1). For each trial, the mouse was placed on the middle of the two objects. At the end of 5 min, the mouse was placed back in its home cage. Thirty minutes after the first trial, each mouse went to trial 2. In this trial, the floor pattern was changed (pattern type 2) and a different object pair (object type 2) was used. At the end of 5 min, the mouse was placed back in its home cage. After a delay of 2 h, each mouse went to trial 3. During this trial, the floor pattern remained the same as in trial 2 (pattern type 2), but an object from trial 1 (object type 1) replaced one of the objects used in trial 2, which had now become a novel object for trial 3. The mouse explored for 5 min. Exploration of the novel object was defined as the length of time a mouse's nose was 1 cm away from the object. Data, such as times spent in exploring the novel object (object type 1 on pattern type 2) and the familiar object (object type 2 on pattern type 2) and the total time spent in object exploration in trial 3, were measured. Furthermore, a novel object discrimination index was calculated by using the following formula: the time spent with the novel object/the total object exploration time×100.

Statistical Tests. Data are represented as mean±SEM. Comparison of three or more groups was performed using one-way ANOVA with Tukey's multiple comparison test. Two-way ANOVA with Bonferroni posttests was carried out for the water maze learning test. A $p$ value of less than 0.05 was considered to be statistically significant.

Example 15—Methods and Therapeutic Preparations for the Treatment of Concussion and Sport and Combat Associated Head Injury The present example is presented to demonstrate the utility of the present invention as a treatment for concussion head injuries, such as those typical of sports-related injuries in athletes.

Concussions occur in all sports with the highest incidence in football, hockey, rugby, soccer and basketball. (Br. J Sports Med (2013) 47(1) 15-26.). Therefore, the present preparations of negatively charged extracellular vesicles (n-EVs), may be employed as a tool for assisting those having experienced a concussion. It is expected that administration of the herein described nEV preparations obtained with human source cells and/or human source tissues, as either an intravenous or intranasal pharmaceutical preparation, will serve to halt further tissue/brain damage and/or to more rapidly restore pre-concussion levels of performance.

In some embodiments, the method for treating a patient having had a concussion will follow the following general steps:

Step 1—Determine if the Person has Suffered a Concussion:

As part of the methods for treating concussion in a human, the first step will involve the evaluation and/or examination of the person to determine if they have experienced a concussion. This evaluation may be accomplished using standard techniques known and described in the literature.

By way of example, The pertinent physical examination elements for concussion include evaluation of cranial nerves, manual muscle testing, and deep tendon reflexes; inspecting the head and neck for trauma or tenderness and cervical range of motion; Spurling maneuver; a static or dynamic balance assessment; screening ocular examination; and a mental status examination that includes orientation, immediate and delayed recall, concentration, mood, affect, insight, and judgment. Other examination elements to consider, based on signs, symptoms, or clinical suspicion, include testing of upper motor neurons, cervical strength and proprioception, coordination, pupillary reactivity, and visual acuity; examination of the jaw, temporomandibular joint, and thoracic spine; fundoscopic evaluation; orthostatic vital signs; assessment of dynamic visual acuity; and screening for depression, anxiety, substance abuse disorders, and pre-injury psychiatric difficulties (See Matuszak et al. (2016) Sports Health).

Identifying a person having had a concussion on the field may include examining the person for some of the more obvious symptoms of concussion, which include loss of consciousness, unresponsiveness, confusion, amnesia and other concerning symptoms that will be readily apparent to, for example, a sports team official, sports coach, attending physician, nurse, or other medical and/or quasi medical related personnel.

Some of the more common and specific approaches for evaluating initial concussion in a person are presented below.

SIDELINE EVALUATION AND MANAGEMENT: Initial assessment of a concussion should be guided by a symptoms checklist, cognitive evaluation (including orientation, past and immediate memory, new learning and concentration), balance tests and further neurological physical examination. While standardized sideline tests are a useful framework for examination, the sensitivity, specificity, validity and reliability of these tests among different age groups, cultural groups and settings is largely undefined. Their practical usefulness with or without an individual baseline test is also largely unknown. Balance disturbance is a specific indicator of a concussion, but not very sensitive. Balance testing on the sideline may be substantially different than baseline tests because of differences in shoe/cleat-type or surface, use of ankle tape or braces, or the presence of other lower extremity injury. Imaging is reserved for athletes where intracerebral bleeding is suspected. There is no same day return to play (RTP) for an athlete diagnosed with a concussion. Athletes suspected or diagnosed with a concussion should be monitored for deteriorating physical or mental status.

NEUROPSYCHOLOGICAL TESTING: Neuropsychological (NP) tests are an objective measure of brain-behaviour relationships and are more sensitive for subtle cognitive impairment than clinical exam. ▶ Most concussions can be managed appropriately without the use of NP testing. Computerized neuropsychological (CNP) testing should be interpreted by healthcare professionals trained and familiar with the type of test and the individual test limitations, including a knowledgeable assessment of the reliable change index, baseline variability and false-positive and false-negative rates. Paper and pencil NP tests can be more comprehensive, test different domains and assess for other conditions which may masquerade as or complicate assessment of concussion. NP testing should be used only as part of a comprehensive concussion management strategy and should not be used in isolation. The ideal timing, frequency and type of NP testing have not been determined. In some cases, properly administered and interpreted NP testing provides an added value to assess cognitive function and recovery in the management of sports concussions. It is unknown if use of NP testing in the management of sports concussion helps prevent recurrent concussion, catastrophic injury or long-term complications. Comprehensive NP evaluation is helpful in the post-concussion management of athletes with persistent symptoms or complicated courses.

Concussion symptoms should be resolved before returning to exercise. A RTP progression involves a gradual, step-wise increase in physical demands, sports-specific activities and the risk for contact. If symptoms occur with activity, the progression should be halted and restarted at the preceding symptom-free step. RTP after concussion should occur only with medical clearance from a licensed healthcare provider trained in the evaluation and management of concussions. SHORT-TERM RISKS OF PREMATURE RTP: The primary concern with early RTP is decreased reaction time leading to an increased risk of a repeat concussion or other injury and prolongation of symptoms. LONG-TERM EFFECTS: There is an increasing concern that head impact exposure and recurrent concussions contribute to long-term neurological sequelae. Some studies have suggested an association between prior concussions and chronic cognitive dysfunction. Large-scale epidemiological studies are needed to more clearly define risk factors and causation of any long-term neurological impairment.

Step 2—Administer an Effective Dose of the nEV Preparation of the Person Identified as Having had a Concussion.

Using any of the above modalities for identifying a concussion has occurred in a person, or any other standard and accepted modality for identifying concussion, the identified person should be administered an appropriate dosage of a pharmaceutical preparation of the nEVs described herein. The particular dose or doses of the pharmaceutical preparation, as well as the schedule of treatment of the person, will vary with the particular person, and will be dictated by the attending physician. However, as part of the presently disclosed methods, the person identified as having experienced a concussion will be administered at least one dose of the n-EVs. Repeat doses may be administered where it is determined that the person is demonstrating an improvement in his/her post-concussion condition.

Step 3—Identifying an Improvement in the Post-Concussion nEV Treated Person to Identify a Person Having Lessened and/or Ameliorated Immediate Signs of Concussion.

Parameters that may be used to identify an improvement of the post-concussion condition of a person after having received a dose and/or treatment regimen of the nEVs may include, for example, regaining conscious, balance, normal speaking ability, etc., I the person The preparation should not be given if there is any reason to expect the person may exhibit an allergic or other adverse reaction to the preparation (such as an allergic reaction), or if the person's condition appears to deteriorate in any way after a first dose of the nEV pharmaceutical preparation is given.

These and other techniques and methods of treatment are well known to those of skill in the art, and may be adapted by the skilled physician for a particular patient pathology without an undue amount of experimental trial and error.

All publications and patents mentioned in the above specification are herein incorporated by reference.

BIBLIOGRAPHY

The following references are specifically incorporated herein by reference:
(1) Crouch, Deborah, "Ocular Therapeutics using Embryonic Stem Cell Microvesicles." U.S. Pub. 20150079047, Mar. 19, 2015.
(2) Kosson, Rosanne, "Pharmaceutical Product for Preventing or Treating Alzheimer's Disease." U.S. Pub. 20140341882, Nov. 20, 2014.
(3) White, Douglas F., "Methods of Use of Culture Supernatant Obtained from Mesenchymal Stem Cells from Dogs and Cats for Treatment of Organ Dysfunction." U.S. Pub. No. 20140314872, Oct. 23, 2014.

(4) Ziska, Suzanne E., "De Novo Anembryonic Trophoblast Vesicles and Methods of Making and Using Them." U.S. Pub. No. 20130287822, Oct. 31, 2013.
(5) Belyayskyi, Michail A., "Therapeutic Vesicles." U.S. Pub. No. 20120093885, Apr. 19, 2012.
(6) Huang, Dong-Ming, "Red Blood Cell-Derived Vesicles as a Nanoparticle Drug Delivery System." U.S. Pat. No. 8,329,161, Dec. 11, 2012.
(7) Watanabe J, Shetty A K, Hattiangady B, Kim D K, Foraker J E, Nishida H, Prockop D J. Neurobiol Dis., 59:86-99.
(8.) Viswanathan S, Keating A, Deans R, Hematti P, Prockop D, Stroncek D F, Stacey. G, Weiss D J, Mason C, Rao M S. (2014) *Stem Cells Dev.*
(9) Reger R L, Prockop D J., (2014), Stem Cells Transl Med. (5):632-5.
(10) Lee R H, Yu J M, Foskett A M, Peltier G, Reneau J C, Bazhanov N, Oh J Y, Prockop, D J. (2014), Proc Natl Acad Sci USA., 111(47):16766-71.
(11) Prockop D J. Science. 1997, 276(5309):71-4. Review. PubMed PMID: 9082988.
(12) Huang, Dong-Ming, "Red Blood Cell-Derived Vesicles as a Nanoparticle Drug Delivery System." U.S. Pub. 20090274630, Nov. 5, 2009.
(13) Sahoo, Susmita, "Therapeutic Vesicles." U.S. Pub. 20120093885, Apr. 19, 2012.
(14) Robins, Jared, "De Novo Anembryonic Trophoblast Vesicles and Methods of Making and Using Them." U.S. Pub. 20130287822, Oct. 31, 2013.
(15) Klingemann, Hans, "Methods of Use of Culture Supernatant Obtained from Mesenchymal Stem Cells from Dogs and Cats for Treatment of Organ Dysfunction." U.S. Pub. 20140314872, Oct. 23, 2014.
(16) Ochiya, Takahiro, "Pharmaceutical Product for Preventing or Treating Alzheimer's Disease." U.S. Pub. 20140341882, Nov. 20, 2014.
(17) Farber, Debora B., "Ocular Therapeutics Using Embryonic Stem Cell Microvesicles." U.S. Pub. 20150079047, Mar. 19, 2015.
(18) Kim, Dong-ki, et al., (2016) PNAS. 113 (1): 170-175.
(19) Maas Al, Stocchetti N, Bullock R (2008) *Lancet Neurol* 7(8):728-741.
(20) Heneka M T, Kummer M P, Latz E (2014) *Nat Rev Immunol* 14(7):463-477.
(21) Lozano D, et al. (2015) *Neuropsychiatr Dis Treat* 11:97-106.
(22) Reis C, et al. (2015) *Int J Mol Sci* (16(6):11903-11965.
(23) Loane D J, Stoica B A, Faden Al (2015) *Handb Clin Neurol* 127:343-366.
(24) Prockop D J, Kota D J, Bazhanov N, Reger R L (2010) *J Cell Mol Med* 14(9):2190-2199.
(25) Keating A (2012) *Cell Stem Cell* 10(6):709-716.
(26) Kramann R, et al. (2015) *Cell Stem Cell* 16(1):51-66.
(27) Schwarz E J, Alexander G M, Prockop D J, Azizi S A (1999), *Hum Gene Ther* 10(15):2539-2549.
(28) Hofstetter C P, et al. (2002) *Proc Natl Acad Sci USA* 99(4):2199-2204.
(29) Ohtaki H, et al. (2008) *Proc Nat Acad Sci USA* 105(38):14638-14643.
(30) QU C, et al. (2008) *Brain Res* 1208:234-239.
(31) Lim P K, Patel S A, Gregory L A, Rameshwar P (2010) *Curr Med Chem* 17(20):2159-2167.
(32) Joyce N, et al. (2010) *Regen Med* 5(6):933-946.
(33) Uccelli A, Benvenuto F, Laroni A, Giunti D (2011) *Best Pract Res Clin Haematol* 24(1):59-64.
(34) Kocsis J D, Honmou O (2012) *Prog Brain Res* 201: 79-98.
(35) Forostyak S, Jendelova P, Sykova E (2013) *Biochimie* 95(12):2257-2270.
(36) Zhang R, et al. (2013) *J Neuroinflammation* 10:106.
(37) Peng W, et al. (2015) *Stem Cell Res Ther* 6:47.
(38) Prockop D J, Oh J Y (2012), *Mol Ther* 20(1):14-20.
(39) Lee R H, et al. (2009), *Cell Stem Cell* 5(1):54-63.
(40) Oh J Y, et al. (2010), *Proc Natl Acad Sci USA* 107(39): 16875-16880.
(41) Choi H, Lee R H, Bazhanov N, Oh J Y, Prockop D J (2011), *Blood* 118(2):330-338.
(42) Oh J Y, et al. (2012), *Mol Ther* 20(11):2143-2152.
(43) Gibb S L, et al. (2015), *Stem Cells* 33(12):3530-3544.
(44) Yanez-Mo M, et al. (2015), *J Extracell Vesicles* 4:27066.
(45) Lo Cierco A, Stahl P D, Raposo G (2015), *Curr Opin Cell Biol* 35:69-77.
(46) Heldring N, Mager I, Wood M J, LeBlanc K, Andaloussi S E (2015), *Hum Gene Ther* 26(8):506-517.
(47) Gyorgy B, et al. (2015), *Annu Rev Pharmacol Toxicol* 55:439-464.
(48) Zhang Y, et al. (2015), *J Neurosurg* 122(4):856-867.
(49) Phinney D G, et al. (1999), *J Cell Biochem* 75(3):424-436.
(50) Montzka K, et al. (2009), *BMC Neurosci* 10:16.
(51) Siddappa R, Licht R, van Blitterswijk C, de Boer J (2007), *J Ortho Res* 25(B):1029-1041.
(52) Lee R H, et al. (2014), *Proc Natl Acad Sci USA* 111(47):16766-16771.
(53) Oksvoid M P, Neurauter A, Pedersen K W (2015), *Methods Mol Blol* 121B:465-481.
(54) Pati S, et al. (2011), *Stem Cells Dev* 20(1):89-101.
(55) Leutgeb S, Leutgeb J K (2007), *Learn Mem* 14(11): 745-757.
(56) Yassa M A, Stark C E (2011), *Trends Neurosci* 34(10): 515-525.
(57) Sekiya I, et al. (2002), *Stem Cells* 20(6):530-541.
(58) Prockop D J, Keating A (2012), *Stem Cells* 30(6):1051-1052.
(59) Boregowda S V, et al. (2012), *Stem Cells* 30(5):975-987.
(60) Sharma R R, Pollock K, Hubel A, McKenna D (2014), *Transfusion* 54(5):1418-1437.
(61) Liu K D, et al. (2014), *Ann Intensive Care* 4:22.
(62) Sekiya I, Muneta T, Horle M, Koga H (2015), *Clin Orthop Relat Res* 473(7):2316-2326.
(63) Spees J L, Olson S D, Whitney M J, Prockop D J (2006), *Proc Natl Acad Sci USA* 103(50:1283-1288.
(64) Islam M N, et al. (2012), *Nat Med* 18(5):759-765.
(65) Pochampally R R, Smith J R, Ylostalo J, Prockop D J (2004), *Blood* 103(5): 1647-1652.
(66) Vallabhaneni K C, et al. (2015), *Oncotarget* 6(7):4953-4967.
(67) Phinney D G, et al. (2015), *Nat Commun* 6:8472.
(68) Cuiffo B G, et al. (2014), *Cell Stem Cell* 15(6):762-774.
(69) Lee R H, Yu J M, Foskett A M, Peltier G, Reneau J C, Bazhanov N, Oh J Y, Prockop D J. (2014), Proc Natl Acad Sci USA., 111(47):16766-71.
(69) Reger R L, Prockop D J. (2014), Stem Cells Transl Med. 3(5):632-5.

What is claimed is:

1. A method for improving pattern separation function and spatial learning ability in a human subject subsequent to a traumatic brain injury (TBI) comprising:

(a) providing a base-line separation function and spatial learning ability measurement of a traumatic brain injury control subject identified to have had a traumatic brain injury (TBI) to provide base-line traumatic brain injury assessment measurements;
(b) administering a pharmaceutically acceptable preparation comprising an effective amount of an enriched preparation of negatively charged human extracellular vesicles (n-EVs) that do not express surface epitope CD9 (CD9−) to the human subject having had traumatic brain injury to provide a treated subject;
(c) assessing the treated subject for separation function and spatial learning ability to provide post-treatment assessment measurements, and comparing the post-treatment assessment measurements to the base-line traumatic brain injury assessment measurements; and
(d) identifying the treated subject having improved pattern separation function and spatial learning ability where the post-treatment assessment measurements are improved compared to the base-line assessment measurements.

2. The method of claim 1, wherein the enriched population of negatively charged extracellular vesicles (n-EVs) comprises about 30 g of protein and $15 \times 10^9$ negatively charged extracellular vesicles (n-EVs) by weight of the preparation.

3. The method of claim 1, wherein the negatively charged extracellular vesicles (n-EVs) have a mean size of about 80 nm to about 250 nm.

4. The method of claim 1, wherein the pharmaceutically acceptable preparation is suitable for intravenous administration or intranasal administration.

5. The method of claim 1, wherein the pharmaceutically acceptable preparation comprises a therapeutically active agent or a biologically active agent.

6. The method of claim 1, wherein the negatively charged extracellular vesicles (n-EVs) lack a combination of two or more of the surface epitopes selected from the group consisting of: CD29, CD44, CD49c, CD49f, CD59, CD73, CD90, CD105, and CD166.

7. The method of claim 1, wherein the negatively charged extracellular vesicles (n-EVs) comprise at least about 50% by volume of the pharmaceutically acceptable preparation.

8. The method of claim 1, wherein the pharmaceutically acceptable preparation comprises mature TSG-6 mRNA, cytokines, micro-RNA and mitochondria.

9. The method of claim 1, wherein the pharmaceutically acceptable preparation comprises an injectable preparation.

10. The method of claim 1, wherein the negatively charged extracellular vesicles (n-EVs) are CD63+ and CD105−.

* * * * *